United States Patent
Talton et al.

(10) Patent No.: US 11,993,609 B2
(45) Date of Patent: *May 28, 2024

(54) COMPOSITIONS AND METHODS FOR ORAL DELIVERY OF CRYSTALLINE PRX-3140 POTASSIUM SALT

(71) Applicant: Nanopharmaceutics, Inc., Alachua, FL (US)

(72) Inventors: James David Talton, Alachua, FL (US); Mianji Zhang, Alachua, FL (US); Lianhao Zhang, Alachua, FL (US); Otto Joseph Geoffroy, Alachua, FL (US); Daniel Gerard Morgan, Alachua, FL (US)

(73) Assignee: Nanopharmaceutics, Inc., Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/195,506

(22) Filed: May 10, 2023

(65) Prior Publication Data

US 2023/0391791 A1 Dec. 7, 2023

Related U.S. Application Data

(63) Continuation of application No. 17/830,519, filed on Jun. 2, 2022, now Pat. No. 11,725,016.

(51) Int. Cl.
*C07D 495/04* (2006.01)
*A61K 9/00* (2006.01)
*A61K 9/16* (2006.01)
*C07D 497/04* (2006.01)

(52) U.S. Cl.
CPC .......... *C07D 495/04* (2013.01); *A61K 9/0053* (2013.01); *A61K 9/1682* (2013.01); *C07D 497/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,488,736 B2 | 2/2009 | Dhanoa | |
| 7,982,040 B2 | 7/2011 | Dhanoa | |
| 11,725,016 B1 * | 8/2023 | Talton | A61K 9/0053 424/489 |

* cited by examiner

*Primary Examiner* — Brian J Davis
(74) *Attorney, Agent, or Firm* — Finnegan, Henderson, Farabow, Garrett & Dunner LLP

(57) ABSTRACT

The present disclosure addresses this need by providing crystalline fine particle forms of PRX-3140 potassium salt, methods for preparation and the treatment for Alzheimer's disease (AD) and other dementias affecting the cholinergic and/or serotonergic systems including post-traumatic stress disorder (PTSD). In certain aspects, the present disclosure provides novel methods of preparing the compound of Formula I thereof, or PRX-3140 potassium salts, crystalline fine particle forms of PRX-3140 potassium salt, and compositions comprising them. In certain aspects, the present disclosure provides novel crystalline fine particle form of PRX-3140 potassium salt which may provide advantages including improved bioavailability and stability relative to other crystalline or amorphous forms. In other aspects, the present disclosure provides oral dosage forms of crystalline fine particle form of PRX-3140 potassium salt and excipients with improved stability. In additional aspects, the present disclosure provides novel methods of synthesizing novel crystalline fine particle form of PRX-3140 potassium salt, preparing crystalline PRX-3140 potassium salt particle delivery systems (PDS), and preparing novel final dosage forms (FDF) of crystalline fine particle PRX-3140 potassium salt. In certain aspects, the present disclosure provides novel crystalline forms of fine particle PRX-3140 potassium salt which may provide advantages including improved bioavailability and stability relative to other crystalline or amorphous forms.

28 Claims, 12 Drawing Sheets

Formula I: ##STR00001##

Formula II: ##STR00002##

Formula III: ##STR00003##

FIGURE 3: Example 2
A
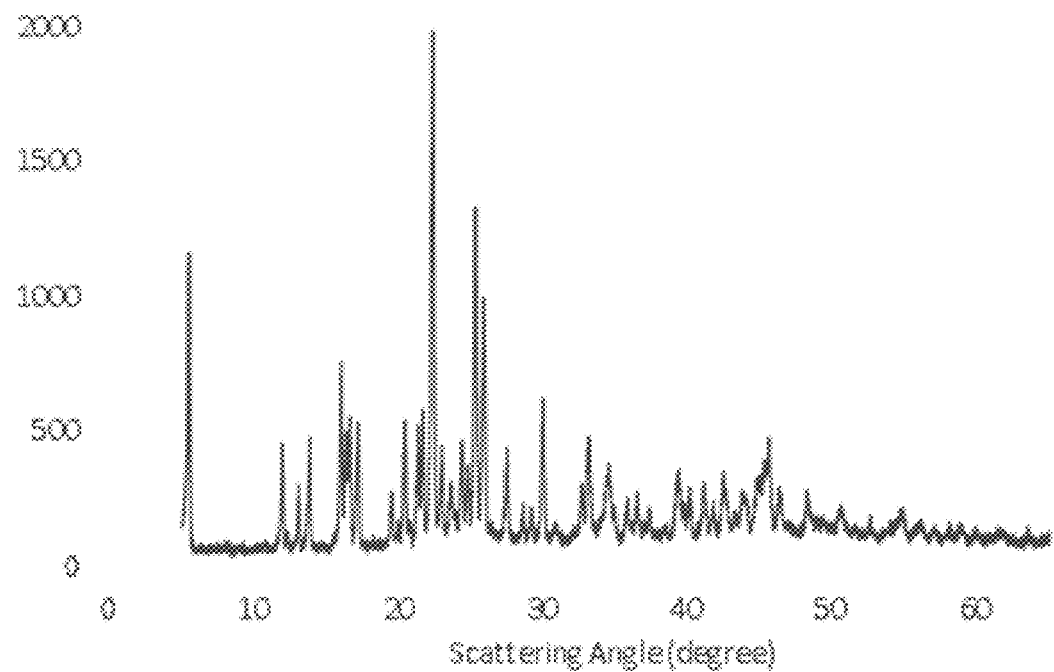
B
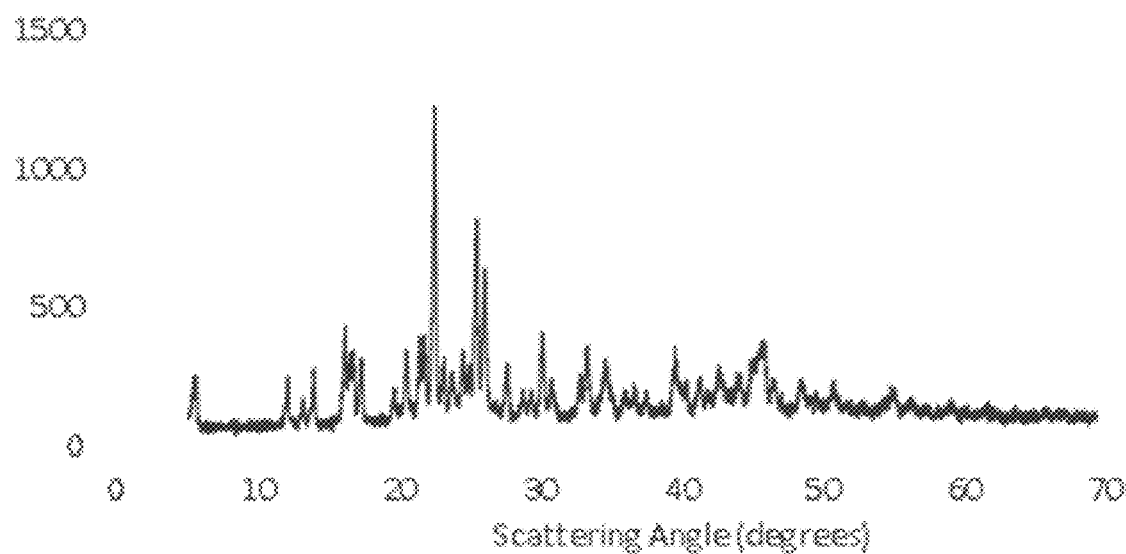

FIGURE 4: Example 3
A
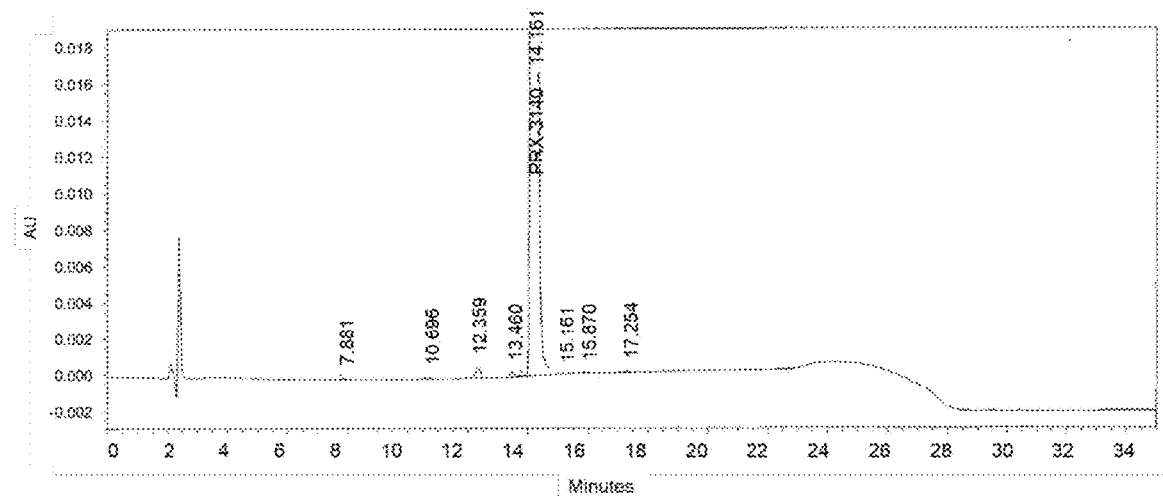
B
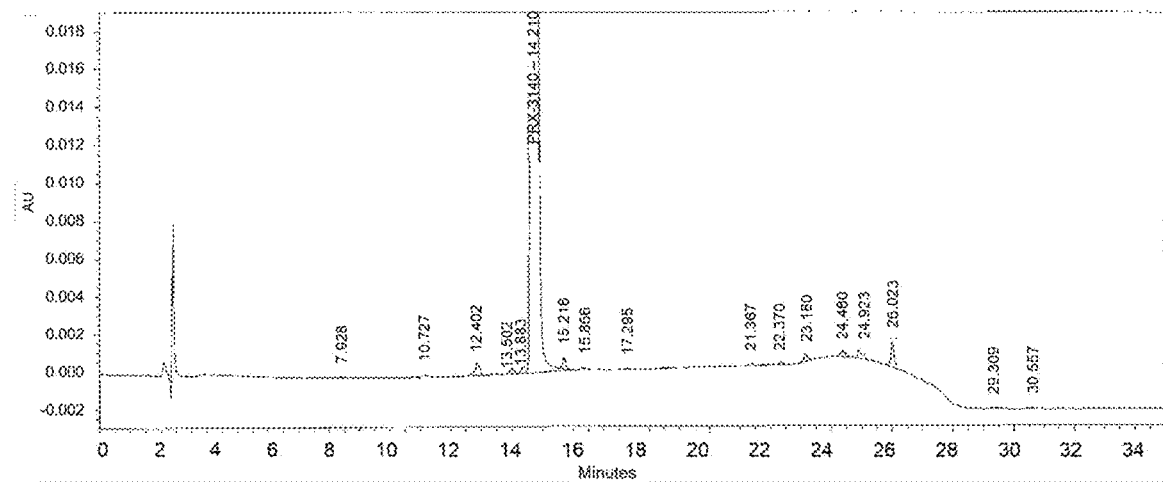

FIGURE 5: Example 4
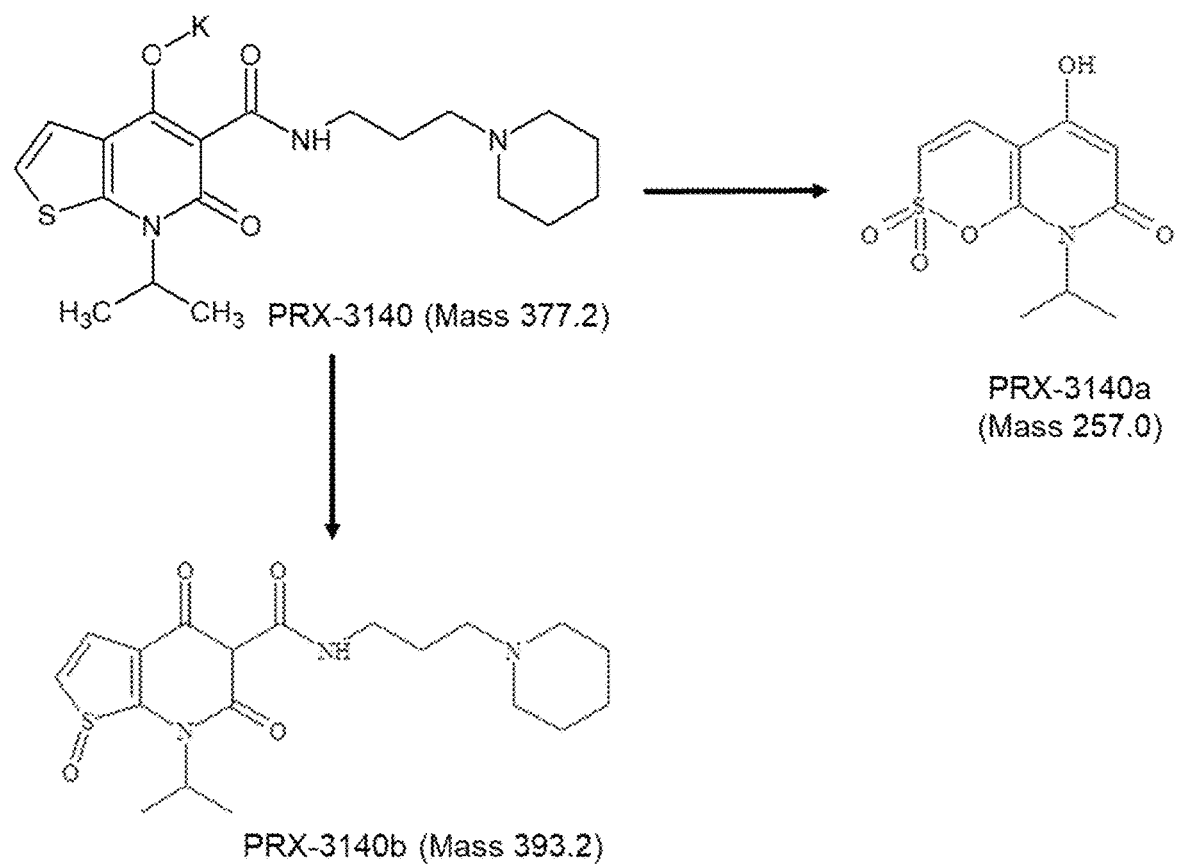

FIGURE 6: Example 4
A
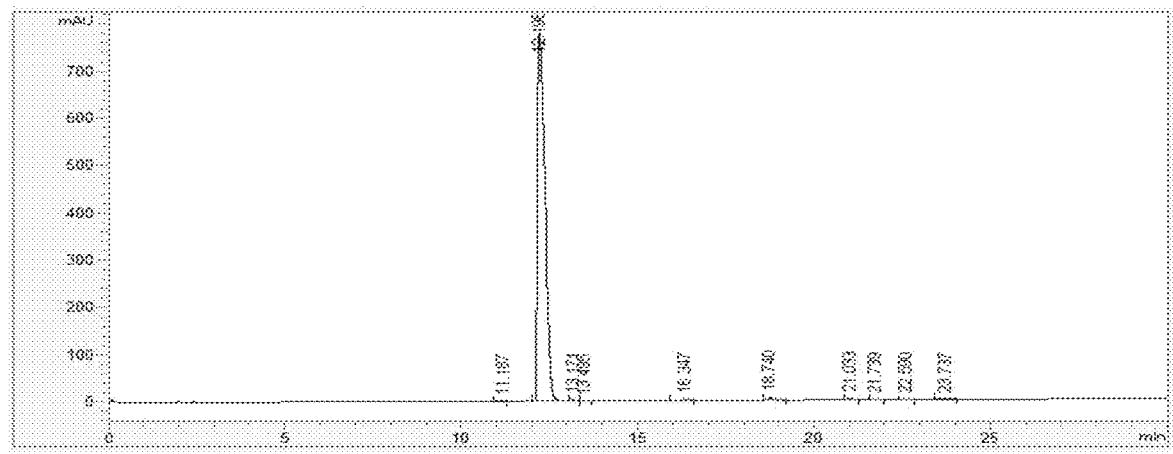
B
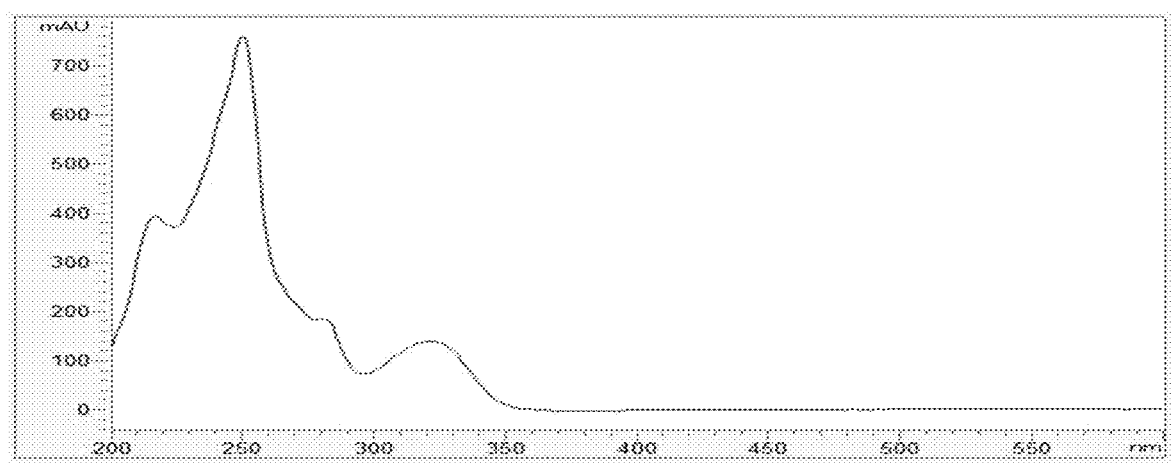
C
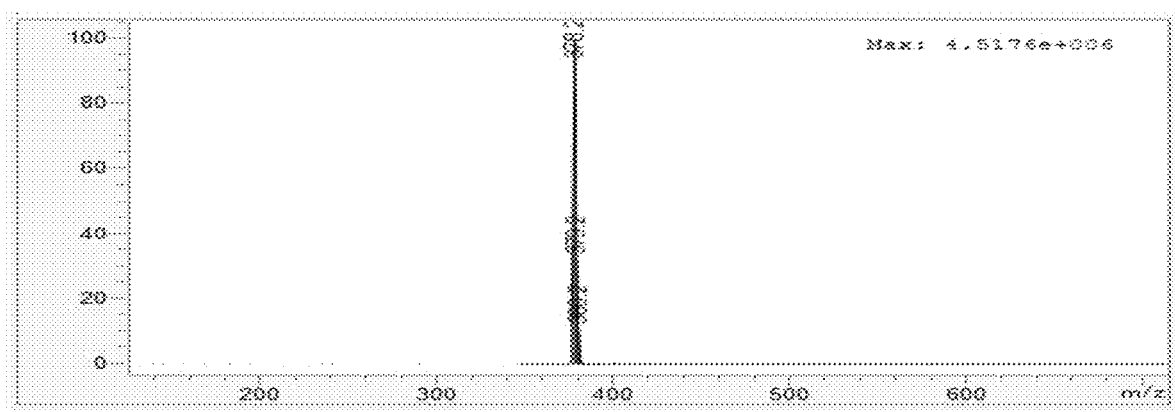

FIGURE 7: Example 4
A
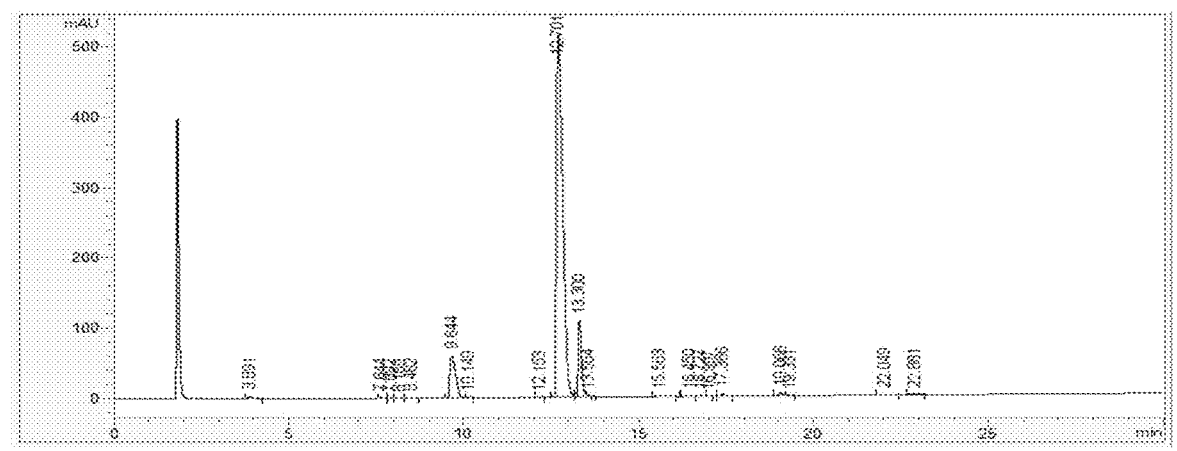
B
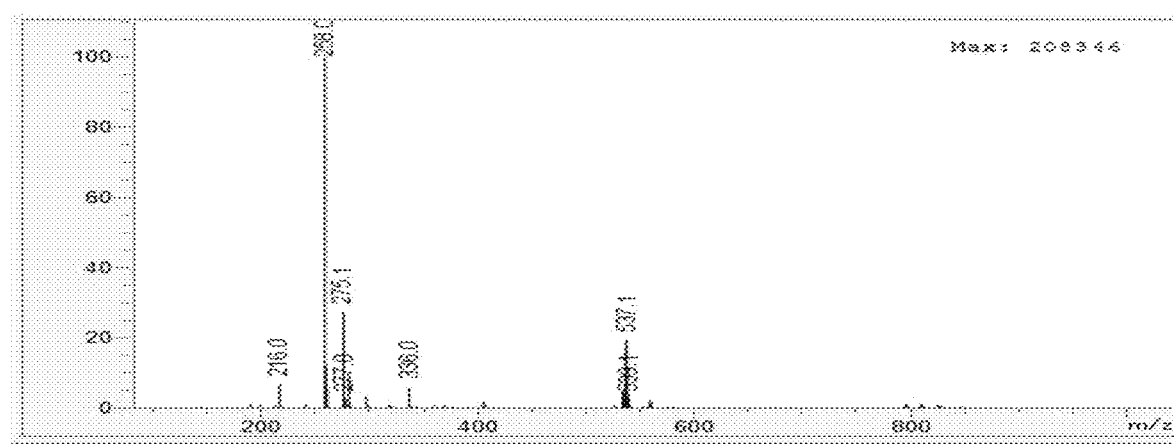
C
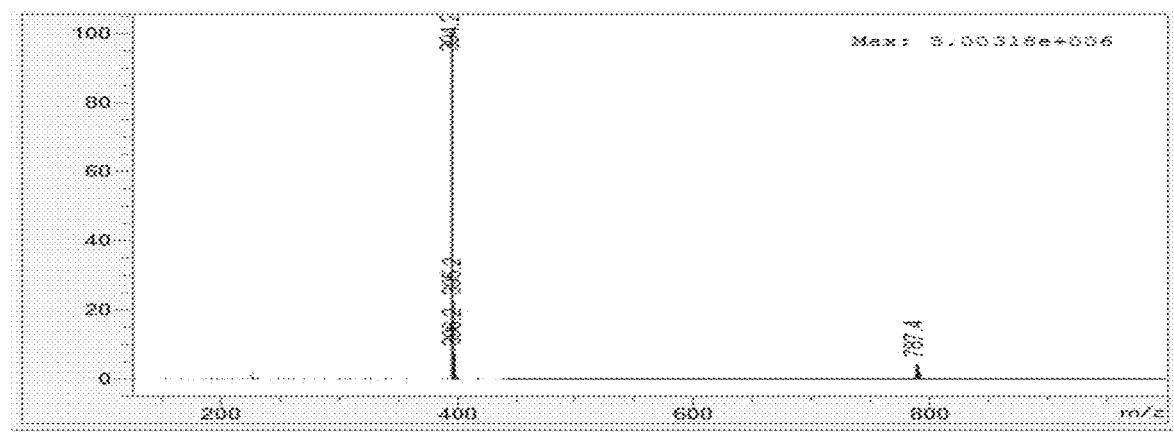

FIGURE 8: Example 5
A
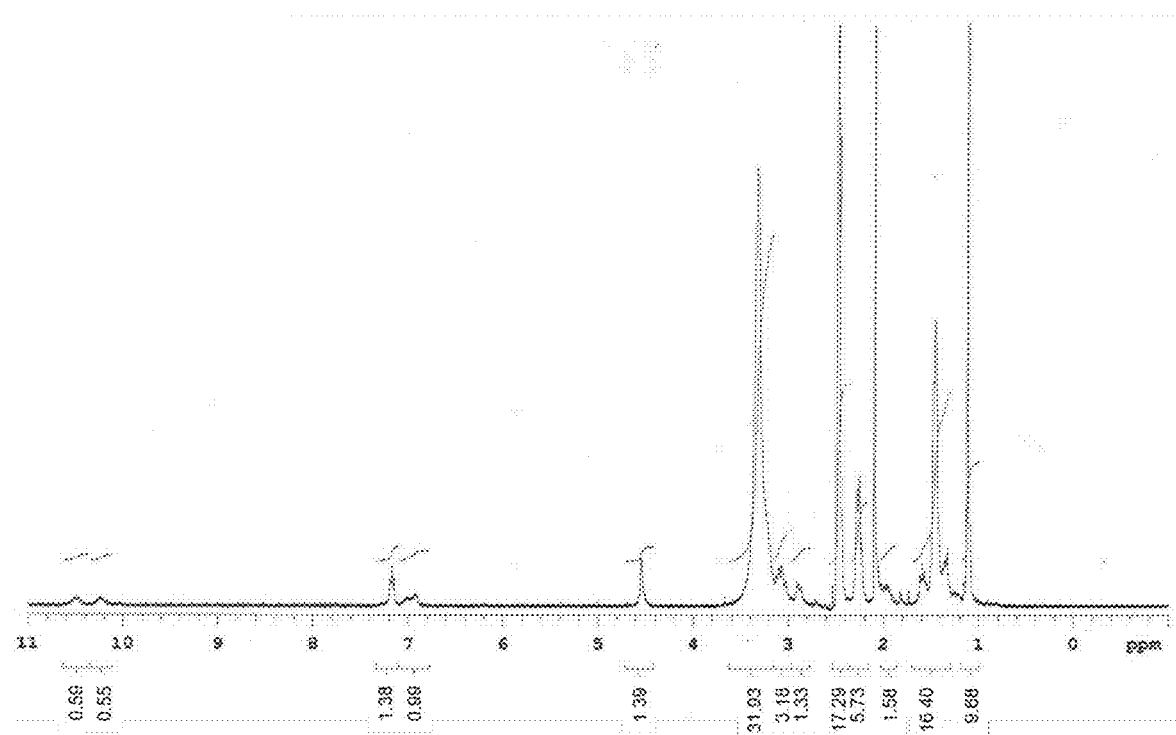
B
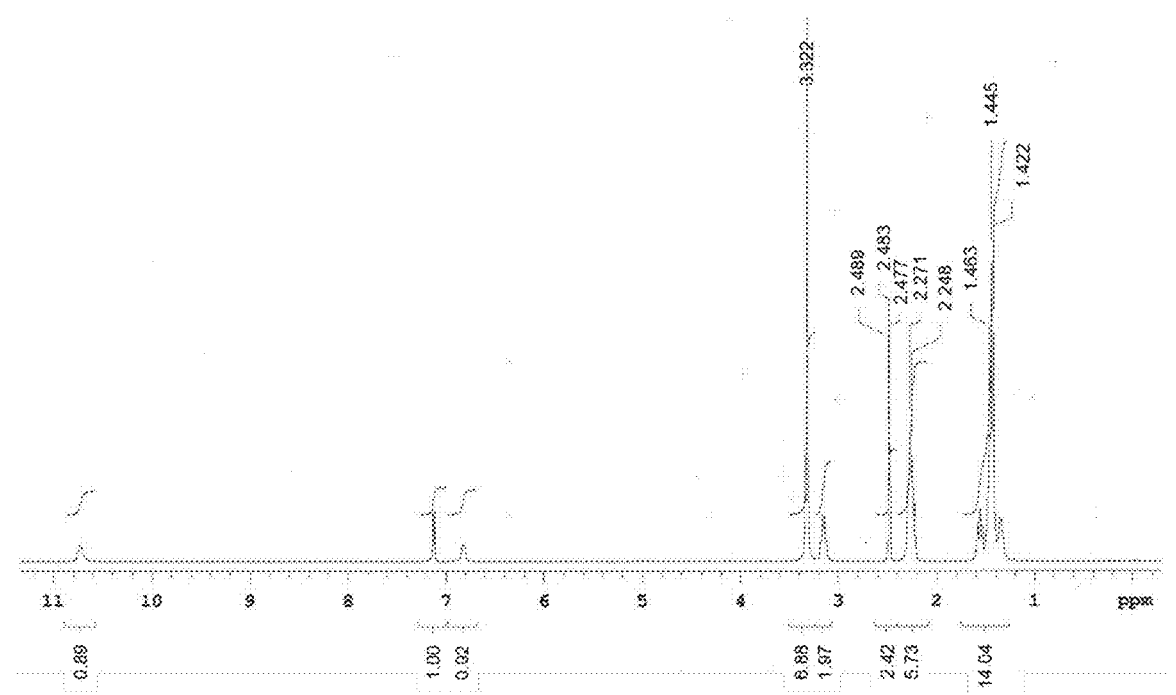

FIGURE 9: Example 5
A
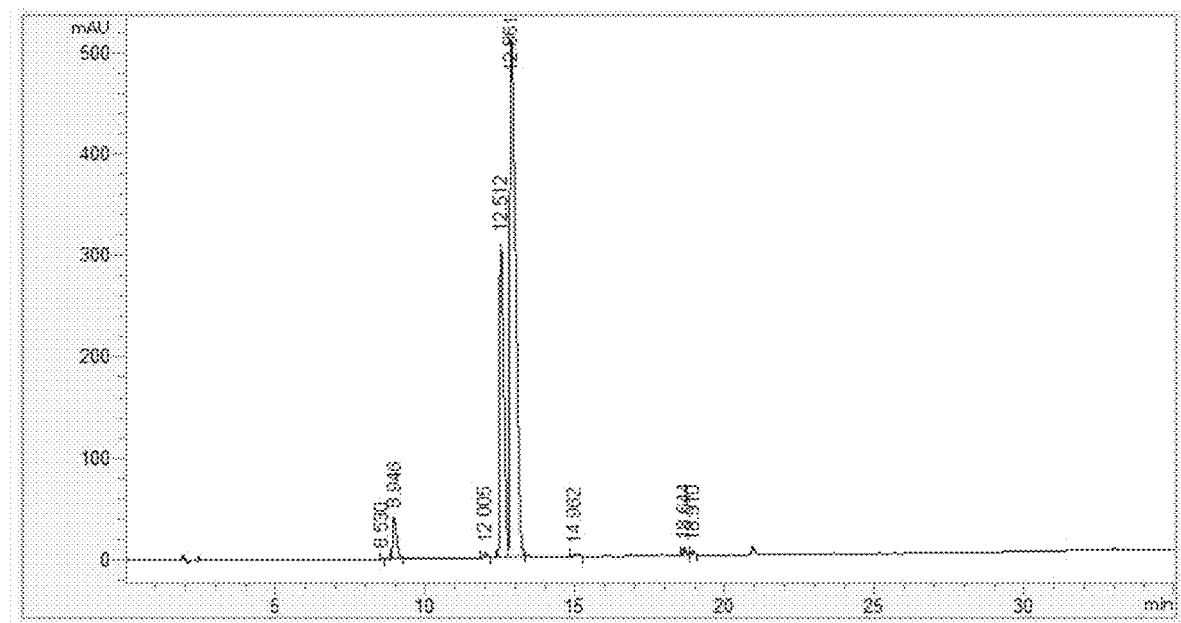
B
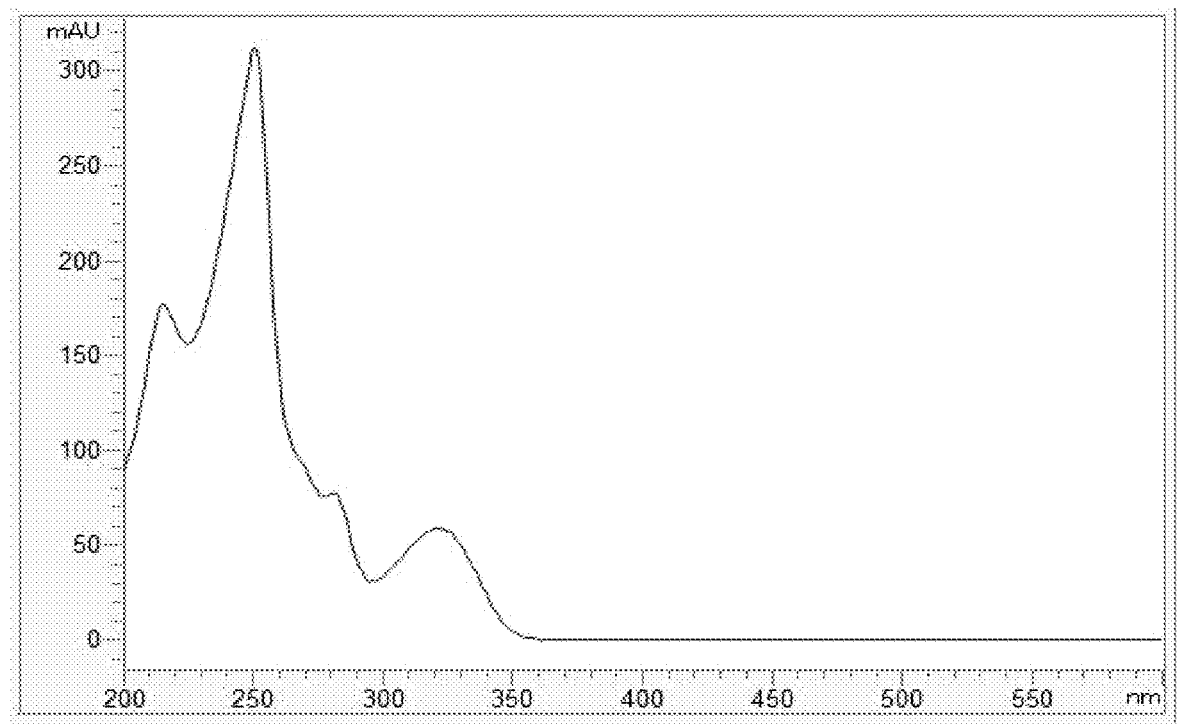

FIGURE 10: Example 5
A
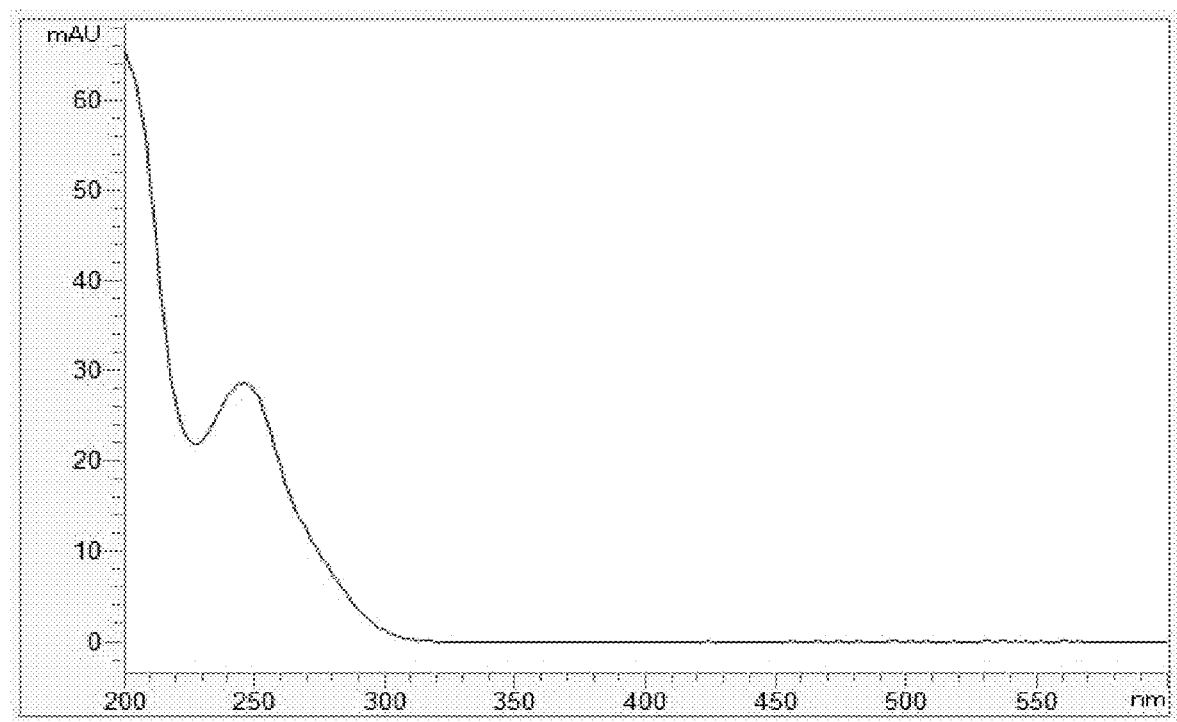
B
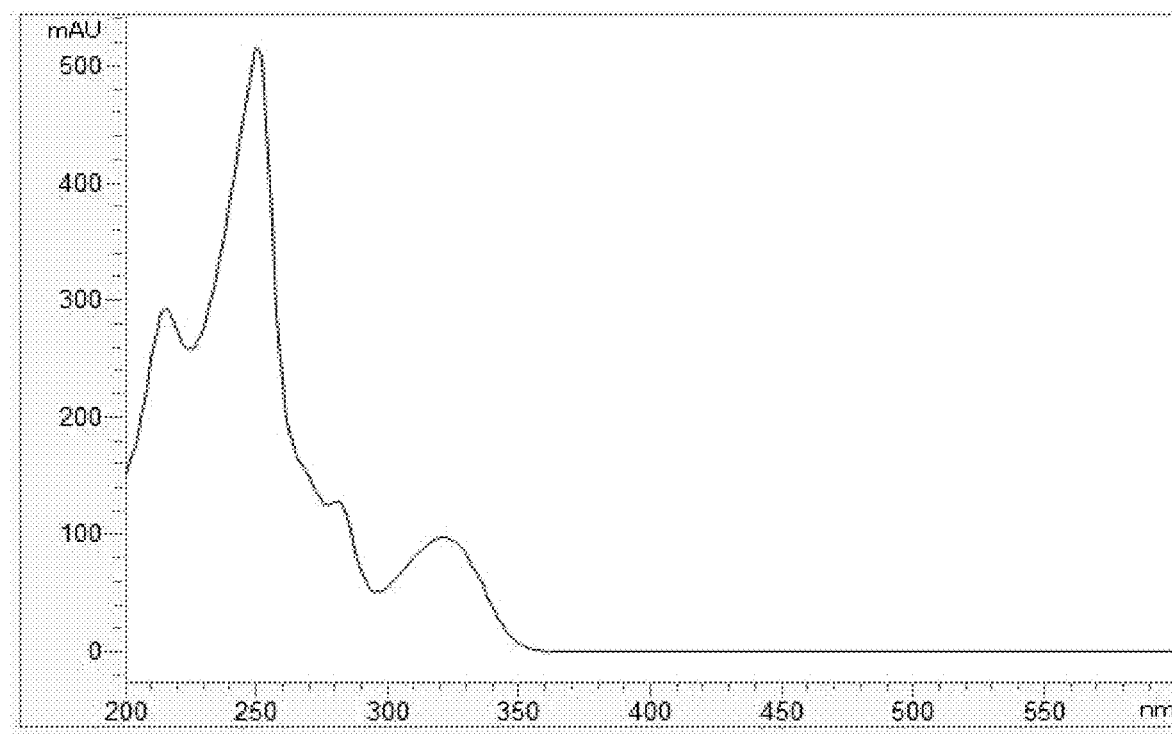

FIGURE 11: Example 5
A
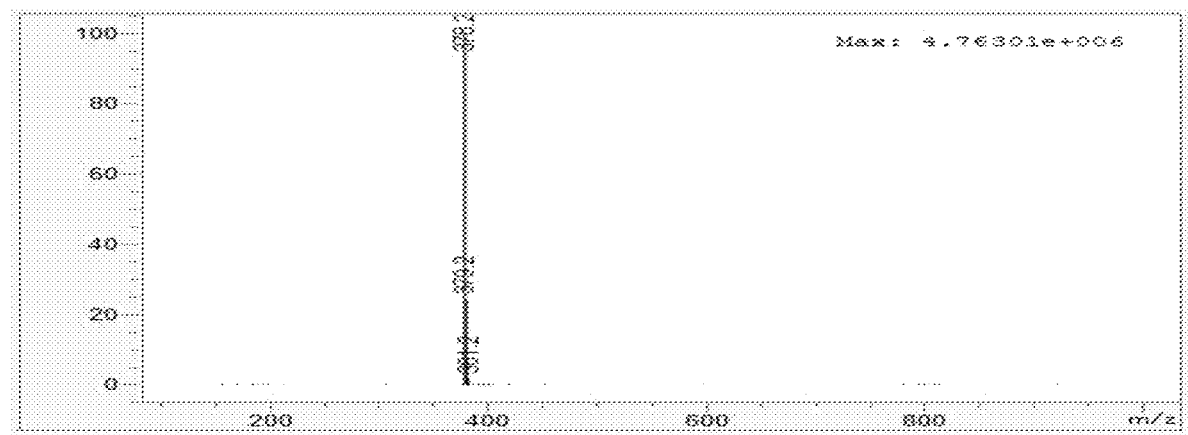
B
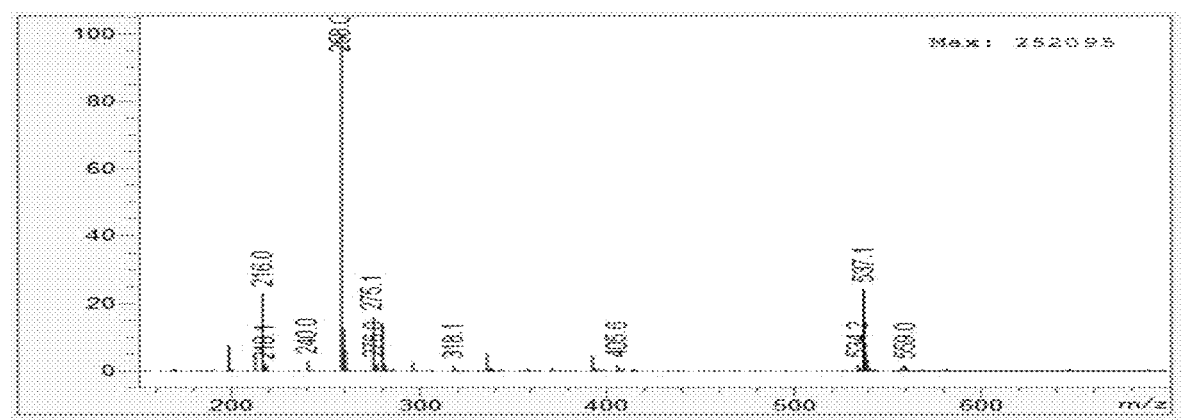
C
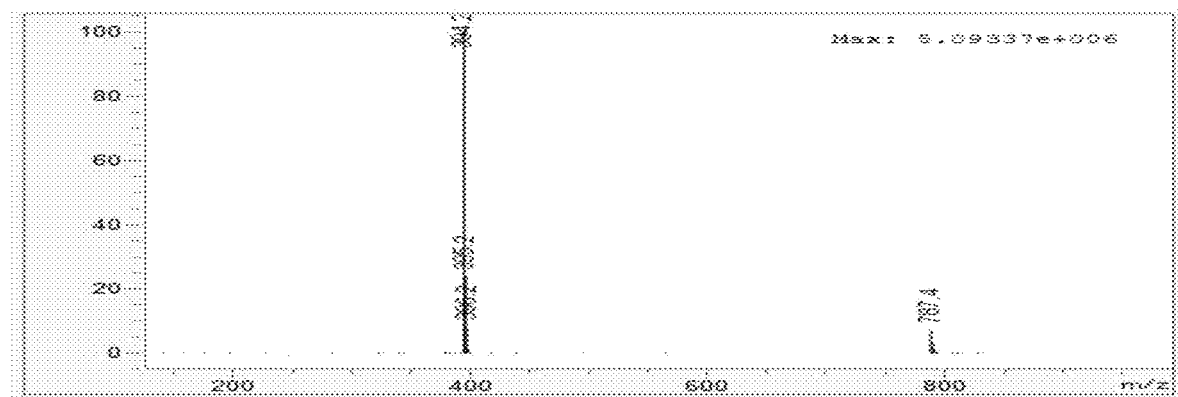

FIGURE 12: Example 6
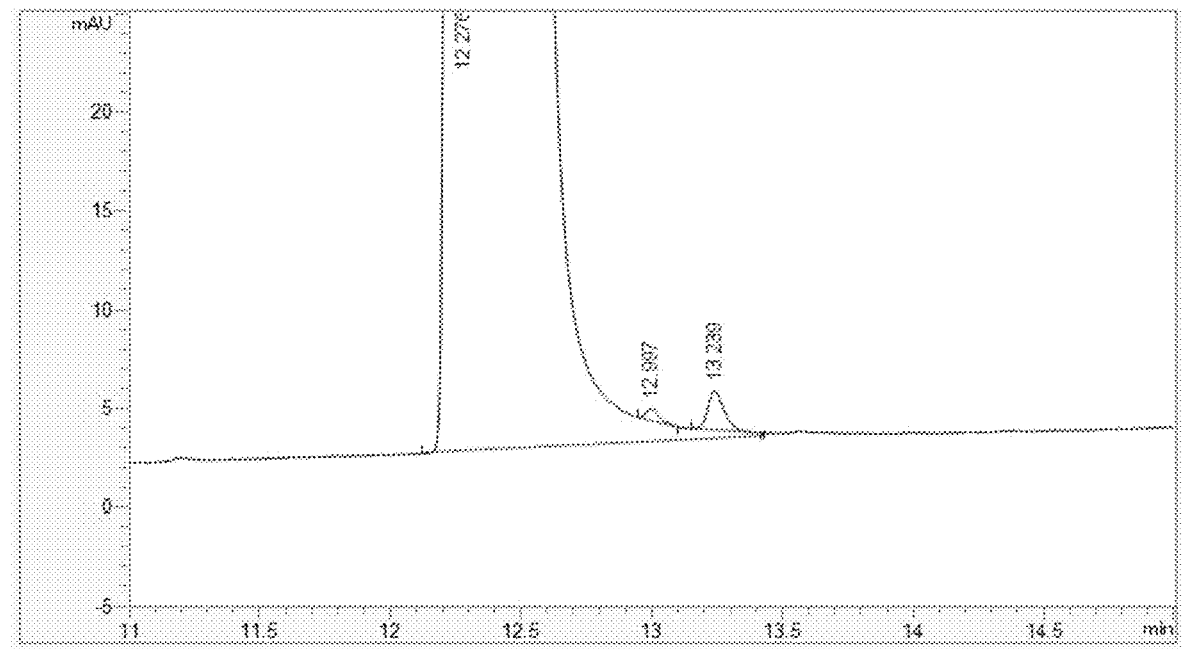
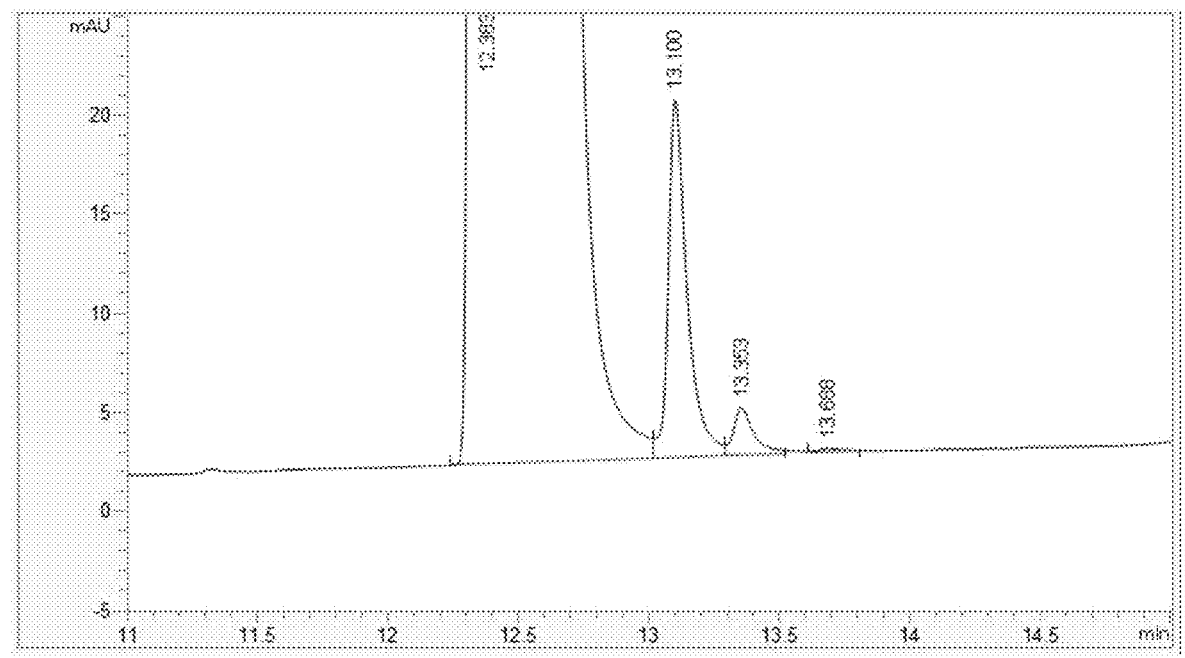

COMPOSITIONS AND METHODS FOR ORAL DELIVERY OF CRYSTALLINE PRX-3140 POTASSIUM SALT

BACKGROUND

The present disclosure relates generally to a novel crystalline form of a compound of Formula I: ##STR00001##, also referred to as 6,7-Dihydro-4-hydroxy-7-isopropyl-6-oxo-N-(3-(piperidin-1-yl)propyl)thieno[2,3-b]pyridine-5-carboxamide potassium salt or potassium 7-isopropyl-6-oxo-5-(3-piperidin-1-yl-propylcarbamoyl)-6,7-dihydro-thieno[2,3-b]pyridine-4-olate, particle delivery systems of the crystalline compound, methods of preparing such compositions, and therapeutic uses thereof. The compound of the present disclosure was originally described in U.S. Pat. No. 7,488,736 followed by U.S. Pat. No. 7,982,040 as well as foreign patents. The crystalline potassium salt compositions described herein allow the compound to be administered by routes that are non-invasive to patients, such as by oral administration.

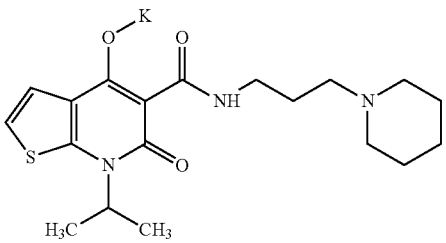

The compound of the present disclosure, referred to in the literature as PRX-3140 or PRX-03140, is a selective partial agonist to the 5-Hydroxytryptamine receptor 4 (5-HT4) and a ligand for the Sigma-1 and Sigma-2 receptors. PRX-3140 is a highly selective and potent (Ki=22-37 nM) 5-HT4R agonist in radioligand binding assays with more than 100-fold difference in affinities compared with all other 5-HT receptors tested. PRX-3140 behaves as a partial agonist in cell lines expressing either the human 5-HT4aR, 5-HT4bR or 5-HT4eR isoforms, stimulating cAMP production to 30%-60% compared to 5-HT. PRX-3140 also demonstrates binding to both the Sigma-1 and Sigma-2 receptors (Ki=79-100 nM and 99-160 nM, respectively) in radioligand binding assays, but demonstrates no significant affinity for more than 50 other receptors tested including GPCRs, ion channels and receptor tyrosine kinases. The specific ligand binding to the receptors is defined as the difference between the total binding and the nonspecific binding determined in the presence of an excess of unlabelled ligand. The inhibition constants (Ki) were calculated from the Cheng Prusoff equation (Ki=IC50/(1-4L/KD)), where L=concentration of radioligand in the assay, Kd=affinity of the radioligand for the receptor and Hill coefficient=1).

PRX-3140 is being developed for Alzheimer's disease (AD) and other dementias affecting the cholinergic and/or serotonergic systems including post-traumatic stress disorder (PTSD). Extensive non-clinical studies have been completed including in vitro and in vivo pharmacology, safety pharmacology, genotoxicity as well as single and repeat dose toxicology studies in two species, rat and beagle dog. Early-stage clinical studies, including safety, tolerability, and pharmacokinetics of PRX-3140 demonstrates high oral bioavailability, as well as safety and efficacy, of the compound up to 250 milligrams. Besides its high oral bioavailability, PRX-3140 achieves a brain/serum partition ratio of 0.93 after 1 hour following oral administration in preclinical studies. PRX-3140 demonstrates high CNS penetration without inducing significant distal gastrointestinal motility observed with gastrointestinally active 5-HT4 agonists (e.g. cisapride, tegaserod).

Oral administration of drugs, such as PRX-3140, is generally preferred over intravenous administration for reasons of patient comfort and compliance. However, many drugs are variably absorbed when delivered orally. There has been substantial effort in the last decade to produce drug particles from 100 nanometers to a few hundred microns because of their improved dissolution properties and ability to be absorbed more efficiently. Through a number of experiments, the present inventors have surprisingly discovered new solid forms of PRX-3140 forms, comprising the fine particle crystalline form of the PRX-3140 potassium salt. This crystal form has unexpectedly good properties and is more suitable for formulation processing, storage, industrial production, and has better bioavailability. Compared with the known solid form of PRX-3140 described in U.S. Pat. No. 7,488,736 followed by U.S. Pat. No. 7,982,040, the fine particle crystalline form of the PRX-3140 potassium salt in present invention have at least one or more superior properties and achieve unexpected effects. Specific improvements are, for example, higher solubility in water, higher dissolution rate, better stability, lower hygroscopicity, better flowability and favorable processing and handling characteristics. Preferably, the new solid form in the present invention has improved stability.

SUMMARY OF THE INVENTION

The present disclosure addresses this need by providing crystalline potassium salt compositions of the compound, methods for preparation and the treatment for Alzheimer's disease (AD) and other dementias affecting the cholinergic and/or serotonergic systems including post-traumatic stress disorder (PTSD). In certain aspects, the present disclosure provides novel methods of preparing the compound of Formula I thereof, or PRX-3140 potassium salts, crystalline fine particle forms of PRX-3140 potassium salt, and compositions comprising them. In certain aspects, the present disclosure provides novel crystalline fine particle form of PRX-3140 potassium salt which may provide advantages including improved bioavailability and stability relative to other crystalline or amorphous forms. In other aspects, the present disclosure provides oral dosage forms of crystalline fine particle form of PRX-3140 potassium salt and excipients with improved stability. In additional aspects, the present disclosure provides novel methods of synthesizing novel crystalline fine particle form of PRX-3140 potassium salt, preparing crystalline PRX-3140 potassium salt particle delivery systems (PDS), and preparing novel final dosage forms (FDF) of crystalline fine particle PRX-3140 potassium salt. In certain aspects, the present disclosure provides novel crystalline forms of fine particle PRX-3140 potassium salt which may provide advantages including improved bioavailability and stability relative to other crystalline or amorphous forms.

In certain aspects, the present disclosure provides a composition comprising a crystalline form of the potassium salt of the compound of Formula I, ##STR00001## shown in FIG. 1.

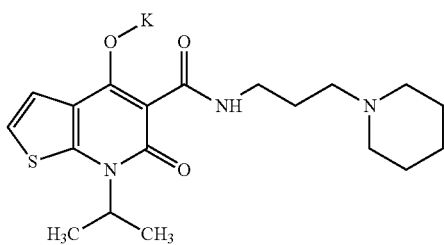

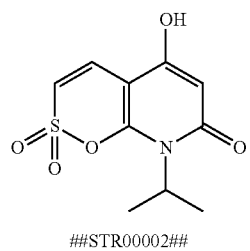

Formula II

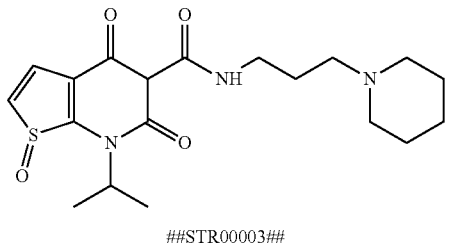

Formula III

In some embodiments, a composition comprising a crystalline form of a compound of Formula I: ##STR00001## and wherein the crystalline form is Form I, characterized by an x-ray powder diffraction pattern comprising major peaks at 22.3+/−0.3 degrees, 25.3+/−0.3 degrees and 5.4+/−0.3 degrees two theta., and optionally further comprising at least one peak selected from 25.8+/−0.3 degrees, 15.9+/−0.3 degrees and 29.9+/−0.3 degrees two theta. In some embodiments, the x-ray powder diffraction pattern further comprises at least one peak selected from 21.6+/−0.3 degrees, 16.5+/−0.3 degrees and 20.3 degrees two theta. The x-ray powder diffraction pattern may further comprise peaks at 21.3+/−0.3 degrees, 17.1+/−0.3 degrees, 16.3+/−0.3 degrees, 33.1+/−0.3 degrees, 45.6+/−0.3 degrees and 13.7+/−0.3 degrees two theta. In some embodiments, crystalline Form I is characterized by an x-ray powder diffraction pattern substantially as set forth in FIGS. 3A and 3B. In some embodiments, greater than 90% by weight of the compound of Formula I in the composition may be crystalline Form I. In some embodiments, the compound of Formula I: ##STR00001## is Form I and is present in an amount ranging from about 0.01% to about 99.99% by mass of the composition. In some embodiments, the composition has an average diameter of less than about 1 mm, 0.5 mm, or 0.3 mm. In some embodiments, the compound is stable for at least 12 months at 5 degrees Celsius and 60% relative humidity or at 25 degrees Celsius and 60% relative humidity. In further embodiments, the formation of degradation products is less than 0.5 weight % per year at 5 degrees Celsius and 60% relative humidity or at 25 degrees Celsius and 60% relative humidity. In additional embodiments, the compound degradation products are Formula II: ##STR00002## 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione and Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide. In further embodiments, the composition is white or light brown color when the composition contains an amount of Formula II: ##STR00002## 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione and Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide less than 0.5 weight %.

In certain embodiments, a particulate delivery system (PDS) is described comprising a crystalline form of a compound of Formula I: ##STR00001## and at least one pharmaceutically acceptable excipient. In certain embodiments, the x-ray powder diffraction pattern further comprises at least one peak selected from 22.3+/−0.3 degrees, 25.3+/−0.3 degrees and 5.4+/−0.3 degrees two theta. In certain embodiments, the x-ray powder diffraction pattern further comprises at least one peak selected from 25.8+/−0.3 degrees, 15.9+/−0.3 degrees and 29.9+/−0.3 degrees two theta. In certain embodiments, the x-ray powder diffraction pattern further comprises at least one peak selected from 21.6+/−0.3 degrees, 16.5+/−0.3 degrees and 20.3 degrees two theta. In certain embodiments, the x-ray powder diffraction pattern further comprises peaks at 25.8+/−0.3 degrees, 15.9+/−0.3 degrees, 29.9+/−0.3 degrees, 21.6+/−0.3 degrees, 16.5+/−0.3 degrees and 20.3 degrees two theta. In certain embodiments, the crystalline form of a compound of Formula I is characterized by an x-ray powder diffraction pattern substantially as set forth in FIG. 3A or FIG. 3B. In certain embodiments, the particulate delivery system contains greater than 90% by weight of the compound of Formula I: ##STR00001## is Form I. In certain embodiments, the particulate delivery system contains the crystalline compound of Formula I: ##STR00001## is Form I and is present in an amount ranging from about 0.01% to about 99.99% by mass, about 10% to about 90% by mass, or about 10% to about 50% by mass. In certain embodiments, the particulate delivery system is formulated for oral, parenteral, or topical delivery. In certain embodiments, the particulate delivery system is formulated for oral delivery as a tablet, a caplet, a capsule, or a pill. In certain embodiments, the particulate delivery system has an average diameter of less than about 1 mm, mm, or 0.3 mm. In certain embodiments, the pharmaceutically acceptable excipient is a polymer, a water-soluble polymer, and is chosen from starch, cellulose, or polyethylene glycol. In certain embodiments, the particulate delivery system includes a second excipient and is chosen from magnesium stearate, stearic acid, hydroxypropyl-beta cyclodextrin, silicon dioxide, or mannitol. In further embodiments, the second excipient is a sugar. In certain embodiments, the particulate delivery system is formulated for oral administration and may comprise 0.01 mg to 200 mg of the compound. In certain embodiments, the particulate delivery system contains the compound and is stable for at least 12 months at 5 degrees Celsius and 60% relative humidity or at 25 degrees Celsius and 60% relative humidity. In further embodiments, the formation of degradation products is less than 0.5 weight % per year at 5 degrees Celsius and 60% relative humidity or at 25 degrees Celsius and 60% relative humidity. In further embodiments, the compound degradation products are Formula II: ##STR00002## 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione and Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide. In further embodiments, the particulate delivery system is white or light brown color when the composition contains an amount of Formula II: ##STR00002## 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione and Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide less than 0.5 weight %.

The present invention also describes methods method of making the particulate delivery system of the compound of the composition, comprising: blending the composition together with an excipient to form a mixture; processing said mixture to form coarse particles having an average diameter ranging from about 0.1 mm to about 5 mm; and grinding or milling said coarse particles to form particles having an average diameter less than about 0.5 mm. In a further embodiment, present invention also describes a method of making the particulate delivery system of the compound of the composition, comprising: blending the composition together with a polymer to form a mixture; processing said mixture to form coarse particles having an average diameter ranging from about 0.1 mm to about 5 mm; and jet-milling said coarse particles to form particles having an average diameter less than about 1 micrometers.

In certain aspects, the present disclosure provides a method of treating Alzheimer's disease (AD) and other dementias affecting the cholinergic and/or serotonergic systems, comprising administering an effective amount of the composition of the compound to a patient in need thereof. In a further embodiment, the present disclosure provides a method of treating post-traumatic stress disorder (PTSD), comprising administering an effective amount of the composition of the compound to a patient in need thereof.

In certain embodiments, the present disclosure provides a method of treating Alzheimer's disease (AD) and other dementias affecting the cholinergic and/or serotonergic systems in a subject, the method comprising administering to the subject a composition comprising a crystalline form of a compound of Formula I: ##STR00001##, wherein at least 90% by weight of the compound of Formula I in the composition is the crystalline form of the compound is Form I, characterized by an x-ray powder diffraction pattern comprising major peaks at 22.3+/−0.3 degrees, 25.3+/−0.3 degrees and 5.4+/−0.3 degrees, and wherein the composition is prepared by blending the composition together with an excipient to form a mixture; processing said mixture to form coarse particles having an average diameter ranging from about 0.1 mm to about 5 mm; and grinding or milling said coarse particles to form particles having an average diameter less than about 500 micrometers.

In one aspect, the present disclosure provides an industrially scalable process for manufacturing a crystalline form of a compound of Formula I: ##STR00001## and wherein the crystalline form is Form I, comprising the steps of:

- reductive amination of methyl 2-aminothiophene-3-carboxylate with sodium triacetoxyborohydride in anhydrous dichloromethane and formic acid under argon followed by work up with potassium hydroxide to obtain methyl 2-iso-propylaminothiophene-3-carboxylate,
- acylation and cyclization of methyl 2-iso-propylaminothiophene-3-carboxylate in pyridine and butyronitrile with methyl malonyl chloride followed by addition of sodium methoxide solution to obtain methyl 4-hydroxy-7-isopropyl-6-oxo-6,7-dihydro-thieno[2,3-b]pyridine-5-carboxylate,
- amidation and of methyl 4-hydroxy-7-isopropyl-6-oxo-6,7-dihydro-thieno[2,3-b]pyridine-5-carboxylate with 3-piperidin-1-yl-propylamine, and acidification with hydrochloric acid to obtain 4-hydroxy-7-isopropyl-6-oxo-6,7-dihydro-thieno[2,3-b]pyridine-5-carboxylic acid (3-piperidin-1-yl-propyl)-amide hydrochloride,
- preparation of 4-hydroxy-7-isopropyl-6-oxo-6,7-dihydro-thieno [2,3-b]pyridine-5-carboxylic acid (3-piperidin-1-yl-propyl)-amide potassium salt by adding 4-hydroxy-7-isopropyl-6-oxo-6,7-dihydro-thieno[2,3-b]pyridine-5-carboxylic acid (3-piperidin-1-yl-propyl)-amide hydrochloride, MTBE, water, potassium hydroxide solution, and sodium bicarbonate to give 4-hydroxy-7-isopropyl-6-oxo-6,7-dihydro-thieno[2,3-b]pyridine-5-carboxylic acid (3-piperidin-1-yl-propyl)-amide followed by dissolution in acetonitrile and addition of potassium hydroxide in water to give crystalline 4-hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt),
- whereas the crystalline form of a compound of Formula I: ##STR00001## and wherein the crystalline form of Form I is obtained by grinding the powder and sieving.

In another aspect, the present disclosure provides a method of making a composition comprising crystalline fine particle Form I of PRX-3140 potassium salt, the method comprising:

- blending crystalline fine particle Form I of PRX-3140 potassium salt together with a stabilizer to form a mixture;
- processing said mixture to form coarse particles having an average diameter ranging from about 0.1 mm to about 5 mm; and
- grinding said coarse particles to form particles having an average diameter ranging from about 0.1 micrometers to about 0.5 mm.

In one aspect, the present disclosure provides an industrially scalable process for manufacturing PRX-3140 potassium salts thereof, comprising the steps of:

- reductive amination of methyl 2-aminothiophene-3-carboxylate with sodium triacetoxyborohydride in anhydrous dichloromethane and formic acid under argon followed by work up with potassium hydroxide to obtain methyl 2-iso-propylaminothiophene-3-carboxylate,
- acylation and cyclization of methyl 2-iso-propylaminothiophene-3-carboxylate in pyridine and butyronitrile with methyl malonyl chloride followed by addition of sodium methoxide solution to obtain methyl 4-hydroxy-7-isopropyl-6-oxo-6,7-dihydro-thieno[2,3-b]pyridine-5-carboxylate, amidation and of methyl 4-hydroxy-7-isopropyl-6-oxo-6,7-dihydro-thieno[2,3-b]pyridine-5-carboxylate with 3-piperidin-1-yl-propylamine, and acidification with hydrochloric acid to obtain 4-hydroxy-7-isopropyl-6-oxo-6,7-dihydro-thieno[2,3-b]pyridine-5-carboxylic acid (3-piperidin-1-yl-propyl)-amide hydrochloride, preparation of 4-hydroxy-7-isopropyl-6-oxo-6,7-dihydro-thieno[2,3-b]pyridine-5-carboxylic acid (3-piperidin-1-yl-propyl)-amide potassium salt by adding 4-hydroxy-7-isopropyl-6-oxo-6,7-dihydro-thieno[2,3-b]pyridine-5-carboxylic acid (3-piperidin-1-yl-propyl)-amide hydrochloride, MTBE, water, potassium hydroxide solution, and sodium bicarbonate to give 4-hydroxy-7-isopropyl-6-oxo-6,7-dihydro-thieno[2,3-b]pyridine-5-carboxylic acid (3-piperidin-1-yl-propyl)-amide followed by dissolution in acetonitrile and addition of potassium hydroxide in water to give crystalline 4-hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt), whereas the crystalline form of a compound of Formula I: ##STR00001## and wherein the crystalline form of Form I is obtained by grinding the powder and sieving.

In some embodiments, the present disclosure provides crystallizing of an input 4-hydroxy-7-isopropyl-6-oxo-6,7-dihydro-thieno[2,3-b]pyridine-5-carboxylic acid (3-piperidin-1-yl-propyl)-amide free base and acetonitrile and addition of potassium hydroxide in water to provide crystalline 4-hydroxy-7-isopropyl-6-oxo-6,7-dihydro-thieno[2,3-b]pyridine-5-carboxylic acid (3-piperidin-1-yl-propyl)-amide potassium salt solid and a mother liquor followed by separation and drying, wherein the crystalline form of a compound of Formula I: ##STR00001## of Form I containing greater than 90% the desired compound. In a further embodiment, the present disclosure provides crystallization by dissolving the input free base in acetonitrile at a first temperature by heating from about 20 degrees Celsius to about 100 degrees Celsius and then cooling the solution to a second temperature. In a further embodiment, the present disclosure provides crystallization by cooling the solution to a temperature ranging from about 0 degrees Celsius to about 20 degrees Celsius. In a further embodiment, the present disclosure provides crystallization by cooling the solution to a temperature ranging from about 0 degrees Celsius to about 20 degrees Celsius for 0.5 hours to 10 days. In a further embodiment, the present disclosure provides crystallization by cooling the solution to a temperature ranging from about 0 degrees Celsius to about 20 degrees Celsius for 2 to 4 hours. In a further embodiment, the present disclosure provides separation of the crystalline solid and the mother liquor may be by filtration, decanting, aspiration, or any suitable method. In yet another further embodiment, the present disclosure provides separation of the crystalline solid and the mother liquor may be by filtration washed with solvent, and dried in vacuo to constant weight. In a further embodiment, the present disclosure provides crystallization using a second solvent, in one embodiment with methyl tert-butyl ether (MTBE). In a further embodiment, the present disclosure provides the crystalline solid washed one or more times with acetonitrile. In a further embodiment, the present disclosure provides the crystalline solid dried under reduced pressure, including at a temperature ranging from about 20 degrees Celsius to about 100 degrees Celsius.

In another embodiment, the present disclosure provides a crystal form of a compound of Formula I: ##STR00001##

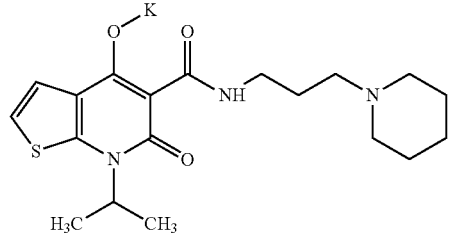

wherein Form I is described with the x-ray powder diffraction pattern further comprises at least one peak selected from 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3 degrees two theta, wherein greater than 90% by weight of the compound of Formula I: ##STR00001## is Form I.

In another embodiment, the present disclosure provides a crystal form of a compound of Formula I: ##STR00001##

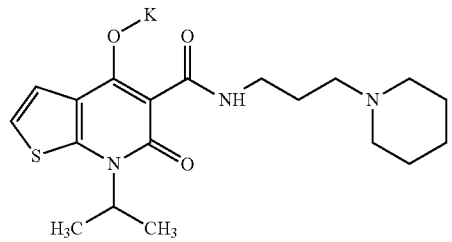

wherein the crystalline form is Form I, characterized by an x-ray powder diffraction pattern further comprises at least one peak selected from 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3+/−0.3 degrees two theta, wherein greater than 90% by weight of the compound of Formula I: ##STR00001## is Form I, wherein the composition has crystalline particles of a compound of Formula I: ##STR00001## with an average diameter of less than about 500 μm, wherein the compound is stable for at least 12 months at 5 degrees Celsius and 60% relative humidity or at 25 degrees Celsius and 60% relative humidity.

In another embodiment, the present disclosure provides methods of making the particulate delivery system of the compound of the composition, comprising: blending the composition together with an excipient to form a mixture; processing said mixture to form coarse particles having an average diameter ranging from about 0.1 mm to about 5 mm; and grinding or milling said coarse particles to form particles having an average diameter less than about 0.5 mm. In a further embodiment, present invention also describes a method of making the particulate delivery system of the compound of the composition, comprising: blending the composition together with a polymer to form a mixture; processing said mixture to form coarse particles having an average diameter ranging from about 0.1 mm to about 5 mm;

and jet-milling said coarse particles to form particles having an average diameter less than about 1 micrometers.

In yet another embodiment, the present disclosure provides a particulate delivery system comprising a crystalline form of a compound of Formula I: ##STR00001## wherein the crystalline form is Form I, characterized by an x-ray powder diffraction pattern comprising major peaks at 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3 degrees two theta and at least one pharmaceutically acceptable excipient,
wherein greater than 90% by weight of the compound of Formula I: ##STR00001## is Form I,
wherein the composition has crystalline particles of a compound of Formula I:
STR00001## with an average diameter of less than about 500 μm,
wherein the compound is stable for at least 12 months at 5 degrees Celsius and 60% relative humidity or at 25 degrees Celsius and 60% relative humidity,
and wherein the particulate delivery system is formulated for oral delivery.

In yet another embodiment, the present disclosure provides an industrially scalable process for manufacturing a crystalline form of a compound of Formula I: ##STR00001## and wherein the crystalline form is Form I, comprising the steps of:
reductive amination of methyl 2-aminothiophene-3-carboxylate with sodium triacetoxyborohydride in anhydrous dichloromethane and formic acid under argon followed by work up with potassium hydroxide to obtain methyl 2-iso-propylaminothiophene-3-carboxylate,
acylation and cyclization of methyl 2-iso-propylaminothiophene-3-carboxylate in pyridine and butyronitrile with methyl malonyl chloride followed by addition of sodium methoxide solution to obtain methyl 4-hydroxy-7-isopropyl-6-oxo-6,7-dihydro-thieno[2,3-b]pyridine-5-carboxylate,
amidation and of methyl 4-hydroxy-7-isopropyl-6-oxo-6,7-dihydro-thieno[2,3-b]pyridine-5-carboxylate with 3-piperidin-1-yl-propylamine, and acidification with hydrochloric acid to obtain 4-hydroxy-7-isopropyl-6-oxo-6,7-dihydro-thieno[2,3-b]pyridine-5-carboxylic acid (3-piperidin-1-yl-propyl)-amide hydrochloride,
preparation of 4-hydroxy-7-isopropyl-6-oxo-6,7-dihydro-thieno[2,3-b]pyridine-5-carboxylic acid (3-piperidin-1-yl-propyl)-amide potassium salt by adding 4-hydroxy-7-isopropyl-6-oxo-6,7-dihydro-thieno[2,3-b]pyridine-5-carboxylic acid (3-piperidin-1-yl-propyl)-amide hydrochloride, MTBE, water, potassium hydroxide solution, and sodium bicarbonate to give 4-hydroxy-7-isopropyl-6-oxo-6,7-dihydro-thieno[2,3-b]pyridine-5-carboxylic acid (3-piperidin-1-yl-propyl)-amide followed by dissolution in acetonitrile and addition of potassium hydroxide in water to give crystalline 4-hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt),
whereas the crystalline form of a compound of Formula I: ##STR00001## and wherein the crystalline form of Form I is obtained by grinding the powder and sieving, wherein crystallization is performed by cooling the solution to a temperature ranging from about 0 degrees Celsius to about 20 degrees Celsius for 2 to 4 hours., wherein the crystalline solid is dried under reduced pressure at a temperature ranging from about 20 degrees Celsius to about 100 degrees Celsius, wherein the crystalline form is Form I is obtained by grinding the powder and sieving, and wherein the crystalline form of a compound of Formula I: ##STR00001## of Form I containing greater than 90% the desired compound.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 is the XRD pattern of Form I of (A) Example 1 crystalline fine particle Form I of PRX-3140 potassium salt and (B) crystalline fine particle Form I of PRX-3140 potassium salt scale-up batch.

FIG. 4 shows the crystalline fine particle Form I of PRX-3140 potassium salt photostability study HPLC chromatograms as (A) unexposed crystalline fine particle Form I of PRX-3140 potassium salt control sample and (B) crystalline fine particle Form I of PRX-3140 potassium salt photostability exposed sample.

FIG. 5 shows the crystalline fine particle Form I of PRX-3140 potassium salt peroxide degradation products Formula II: ##STR00002## 5-hydroxy-8-(methylethyl)-8-hydro-1,2-oxathiino[6.5-b]pyridine-2,2,7-trione, or 5-hydroxy-8-(propan-2-yl)-2H-2k6-[1,2]oxathiino[6,5-b]pyridine-2,2,7(8H)-trione and Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide.

FIG. 6 is the Example 3 crystalline fine particle Form I of PRX-3140 potassium salt forced degradation study (A) HPLC chromatogram of standard (Control) at 250 nm and (B) UV Spectra of Standard (Control) at 12.2 minutes. Maxima are identified at 220, 250, and 320 nm.

FIG. 7 is the (A) LC-UV chromatogram of crystalline fine particle Form I of PRX-3140 potassium salt Example 4 peroxide sample at 250 nm. Two major impurities at 9.6 and 13.3 minutes. (B) mass spectra of PRX-3140a peroxide sample at 9.6 minutes. [M+H]$^+$ at 258.1 m/z, [M+H+NH3]$^+$ at 275.1 m/z, [M+Na]$^+$ at 280.1 m/z and [2M+Na]$^+$ at 537.1 m/z. (C) mass spectra of PRX-3140b peroxide sample at 13.3 minutes. [M+H]$^+$ at 394.2 m/z and [2M+H]+ at 787.4 m/z.

FIG. 8 is the 1H NMR of (A) the crude product of oxidation of PRX-3140 and (B) unoxidized PRX-3140 potassium salt.

FIG. 9 is the (A) UV Chromatogram PRX-3140 30% Peroxide Sample at 250 nm. (B) UV Spectra of Standard (Control) at 12.5 minutes. Maximums at 220, 250, and 320 nm.

FIG. 10 is the (A) UV Spectra of PRX-3140a at 8.9 minutes. (B) UV Spectra of PRX-3140b at 12.9 minutes.

FIG. 11 is the (A) Mass Spectra at 12.5 min for Parent Molecule, [M+H]$^+$ at 378.2 m/z. (B) Mass Spectra at H202 Sample at 8.9 min and 70V. [M+H]+ at 258.0 m/z, [M+H+NH3]+ at 275.1 m/z, [M+Na]+ at 280.1 m/z and [2M+Na]+ at 537.1 m/z. (C) Mass Spectra at 12.9 min [M+H]+ at 394.2 m/z and [2M+H]+ at 787.4 m/z.

FIG. 12 is the HPLC chromatogram of PRX-3140: Lecithin (50:50) at (A) Time 0 initial sample and (B) 90 day sample, both at 250 nm.

DETAILED DESCRIPTION

I. Terminology

Figure 1:
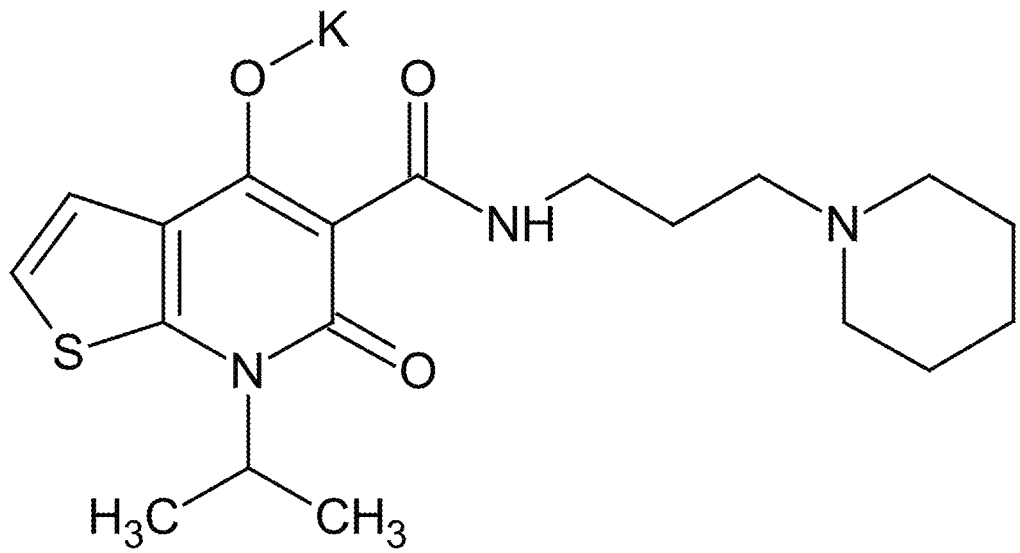
FIG. 1 is the chemical structures of PRX-3140 (Formula I: ##STR00001##), 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione (Formula II: ##STR00002##), and [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide (Formula III: ##STR00003##).
Figure 1:
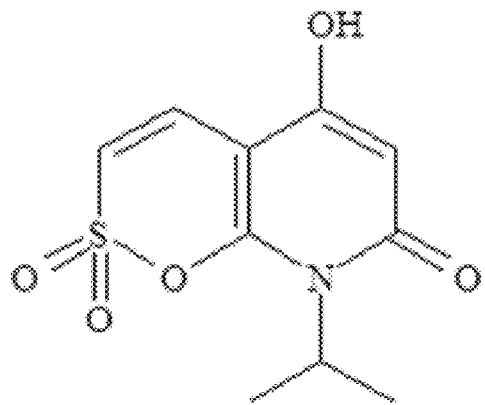
Figure 1:
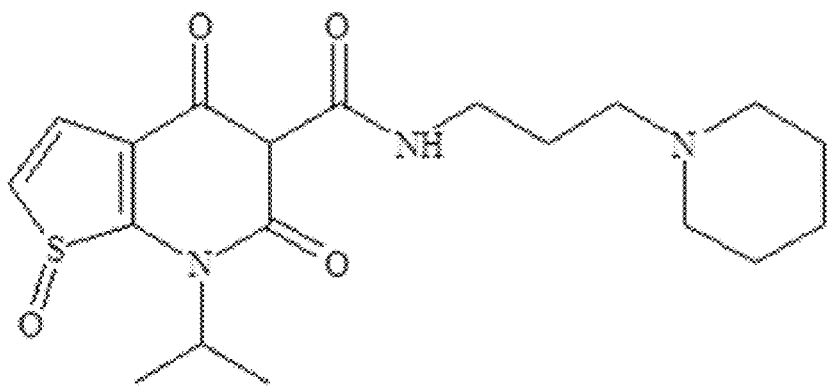

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical, and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include 11C, 13C, and 14C.

The opened ended term "comprising" includes the intermediate and closed terms "consisting essentially of" and "consisting of."

A significant change is any detectable change that is statistically significant in a standard parametric test of statistical significance such as Student's T-test, where $p<0.05$.

II. Synthesis of Crystalline Fine Particle Form I of PRX-3140 Potassium Salt The disclosure includes the following embodiments, which should not be construed as limiting. Rather, these embodiments are exemplary and are provided to describe the invention to those skilled in the art. Like reference numerals refer to like elements throughout.

It has been unexpectedly discovered that dissolution of 4-hydroxy-7-isopropyl-6-oxo-6,7-dihydro-thieno[2,3-b]pyridine-5-carboxylic acid (3-piperidin-1-yl-propyl)-amide free base in acetonitrile and addition of potassium hydroxide in water may be used to obtain crystalline 4-hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt) by heating followed by cooling. This process is distinct from the usual crystallization procedure from U.S. Pat. Nos. 7,488,736 and 7,982,040, which uses potassium tert-butoxide in water mixed with dichloromethane and ethyl acetate, and unexpectedly provides a crystalline solid containing greater than 90% the desired 4-hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt).

In one aspect, the present disclosure provides an industrially scalable process for manufacturing PRX-3140 potassium salts thereof, comprising the steps of: (A) reductive amination of methyl 2-aminothiophene-3-carboxylate with 2,2-dimethoxynpropane using sodium triacetoxyborohydride in anhydrous dichloromethane and formic acid under argon followed by work up with potassium hydroxide to obtain methyl 2-iso-propylaminothiophene-3-carboxylate (3), (B) acylation and cyclization of methyl 2-iso-propylaminothiophene-3-carboxylate (3) in pyridine and butyronitrile with methyl malonyl chloride followed by addition of sodium methoxide solution to obtain methyl 4-hydroxy-7-isopropyl-6-oxo-6,7-dihydro-thieno[2,3-b]pyridine-5-carboxylate (5), (C) amidation of methyl 4-hydroxy-7-isopropyl-6-oxo-6,7-dihydro-thieno[2,3-b]pyridine-5-carboxylate (5) with 3-piperidin-1-yl-propylamine (6), and acidification of the resulting crude PRX-3140 with hydrochloric acid to obtain 4-hydroxy-7-isopropyl-6-oxo-6,7-dihydro-thieno[2,3-b]pyridine-5-carboxylic acid (3-piperidin-1-yl-propyl)-amide hydrochloride (8), and (D) preparation of 4-hydroxy-7-isopropyl-6-oxo-6,7-dihydro-thieno[2,3-b]pyridine-5-carboxylic acid (3-piperidin-1-yl-propyl)-amide potassium salt by adding 4-hydroxy-7-isopropyl-6-oxo-6,7-dihydro-thieno[2,3-b]pyridine-5-carboxylic acid (3-piperidin-1-yl-propyl)-amide hydrochloride (8), MTBE, water, potassium hydroxide solution, and sodium bicarbonate to give 4-hydroxy-7-isopropyl-6-oxo-6,7-dihydro-thieno[2,3-b]pyridine-5-carboxylic acid (3-piperidin-1-yl-propyl)-amide to obtain the free base followed by dissolution in acetonitrile and addition of potassium hydroxide in water to give crystalline 4-hydroxy-7-isopropyl-6-oxo-6,7-dihydro-thieno[2,3-b]pyridine-5-carboxylic acid (3-piperidin-1-yl-propyl)- amide potassium salt (PRX-3140 potassium salt). The crystalline fine particle Form I of PRX-3140 potassium salt is obtained by grinding the powder and sieving.

The initial step in the disclosed process is the crystallizing of an input 4-hydroxy-7-isopropyl-6-oxo-6,7-dihydro-thieno[2,3-b]pyridine-5-carboxylic acid (3-piperidin-1-yl-propyl)-amide free base and acetonitrile and addition of potassium hydroxide in water to provide crystalline 4-hydroxy-7-isopropyl-6-oxo-6, 7-dihydro-thieno[2,3-b]pyridine-5 -carboxylic acid (3-piperidin-1-yl-propyl)-amide potassium salt (PRX-3140 potassium salt) solid and a mother liquor followed by drying, wherein the crystalline solid containing greater than 90% the desired PRX-3140 potassium salt. The crystallization can be performed by dissolving the input free base in acetonitrile at a first temperature by heating and then cooling the solution to a second temperature to effect crystallization. The solution can be held at the second temperature for several hours to allow for adequate crystallization. For example, the input free base can be dissolved in acetonitrile at 45 to 50 degrees Celsius, and then the resulting solution is cooled to 0 to 5 degrees Celsius, and held at the second temperature for 0.5 hours to 10 days, preferably 2 to 4 hours. In some cases, longer holding times at the second temperature may be required. The crystalline solid and the mother liquor may be separated by filtration, decanting, aspiration, or any suitable method. The separated crystalline solid may be washed with a suitable solvent to remove impurities and can be dried with or without heat and/or reduced pressure to remove solvent. Preferably, the crystalline solid is collected by filtration, washed with solvent, and dried in vacuo to constant weight. The separated mother liquor can be concentrated in vacuo to give a solid or a non-solid and can be dried with or without heat and/or reduced pressure to remove solvent. Preferably, the concentrated mother liquor is dried in vacuo to constant weight.

It has been unexpectedly discovered that acetonitrile is a particularly useful solvent for carrying out this step. Other solvents, such as MTBE, may also be used as the second solvent. The crystallization can be performed by dissolving the input crystalline solid in the second solvent at a first temperature of 20 to 100 degrees Celsius and then cooling the solution by 20 to 100 degrees Celsius to a second temperature to effect crystallization. The solution can be held at the second temperature for several hours to allow for adequate crystallization. For example, a solid formed from the concentrated first mother liquor can be dissolved in acetonitrile from 30 to degrees Celsius, preferably from 40 to 60 degrees Celsius, and then the resulting solution is cooled to −10 to 20 degrees Celsius or 0 to 10 degrees Celsius, and held at the second temperature for 0.5 hours to 10 days or 2 to 72 hours. In some cases, longer holding times at the second temperature may be required. The crystalline solid and the mother liquor may be separated by filtration, decanting, aspiration, or any suitable method. The separated crystalline solid may be washed with a suitable solvent to remove impurities and can be dried with or without heat and/or reduced pressure to remove solvent. The separated mother liquor can be concentrated in vacuo to give a solid and can be dried with or without heat and/or reduced pressure to remove solvent. Preferably, the mother liquor is separated from the crystalline solid by aspiration, concentrated and dried in vacuo to constant weight.

III. Crystalline Forms

In certain aspects, the present disclosure provides crystalline fine particle Form I of PRX-3140 potassium salt. The present disclosure further provides pharmaceutical compositions of PRX-3140 potassium salt comprising the crystalline forms described herein. A crystalline form of PRX-3140 potassium salt may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability), manufacturability (e.g., ease of handling, ability to consistently prepare doses of known strength) and stability (e.g., thermal stability, shelf life) of a pharmaceutical drug product or active ingredient. Such variations may affect the preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of PRX-3140 potassium salt may provide advantages such as: improving the manufacturing process of an active agent or the stability or storability of a drug product form of the compound or an active ingredient, and/or having suitable bioavailability and/or stability as an active agent.

The use of certain solvents and fractional crystallization methods has been found to produce different polymorphic forms of PRX-3140 potassium salt, including polymorphic Form I, which may exhibit one or more favorable characteristics described above. The processes for the preparation of the polymorphs described herein, and characterization of these polymorphs are described in greater detail below.

In certain aspects, the present disclosure provides polymorphic Form I of PRX-3140 potassium salt, wherein at least 90% by weight is PRX-3140 potassium salt. In some embodiments, polymorphic Form I exhibits an x-ray diffraction (XRD) pattern substantially as shown in FIG. 3. In some embodiments, polymorphic Form I has an XRD pattern comprising at least two, at least three, at least four, at least five, or at least six of the major peaks as the XRD pattern substantially as shown in FIG. 3. The crystalline structure of the present invention is substantially pure, unitary, and substantially free of any other crystal form or amorphous state. "Substantially pure" in the present invention when used in reference to a new crystal form means that this new crystal form comprises at least 80% (by weight) of the present compound, more preferably at least 90% (by weight), and especially at least 95% (by weight), especially at least 99% (by weight).

The term "substantially as shown in" when referring, for example, to an XRD pattern, includes a pattern that is not necessarily identical to those depicted herein, but that falls within the limits of experimental error or deviations when considered by one of ordinary skill in the art. The relative intensities of XRD peaks can vary, depending upon the particle size, the sample preparation technique, the sample mounting procedure and the particular instrument employed. The crystalline form in the present invention means that the compound is confirmed by the X-ray powder diffraction pattern characterization shown and has a unique and ordered molecular arrangement or configuration within the crystal lattice. It is well known to those skilled in the art that the experimental error depends on the instrument conditions, sample preparation and sample purity. The 2 theta angle of the peaks in the XRD pattern usually varies slightly depending on the instrument and sample. The difference in peak angle may differ by 1 degrees, 0.8 degrees, 0.5 degrees, 0.3 degrees, 0.1 degrees, et according to different instruments, different samples, etc. Generally, the tolerance is +/−0.2 degrees. Therefore, the difference in peak angle cannot be used as the sole criterion. The relative intensity of peaks may vary with samples, sample preparation, and other experimental conditions, so the order of peak intensities cannot be the sole or decisive factor. The influence of experimental factors such as sample height will cause the overall shift of the peak angle, which usually allows a certain shift. Therefore, those skilled in the art can understand that any crystal form having the same or similar characteristic peaks as the X-ray powder diffraction pattern of the present invention belongs to the scope of the present invention. "Single crystalline form" refers to a single crystal form as determined by X-ray powder diffraction.

Moreover, instrument variation and other factors can affect the two theta values. Accordingly, when a specified two theta angle is provided, it is to be understood that the specified two theta angle can vary by the specified value +/−0.5 degrees, such as +/−0.4 degrees, +/−0.3 degrees, +/−0.2 degrees, or +/−0.1 degrees. As used herein, "major peak" refers to an XRD peak with a peak intensity greater than baseline, such as greater than 100 or 500 depending on the baseline noise and other test factors listed above.

In certain aspects, the present disclosure provides at least 90% by weight of PRX-3140 compound of Formula I in the composition is a crystalline form of the potassium salt. Crystalline Form I may be characterized by an x-ray powder diffraction pattern comprising major peaks at 22.3+/−0.3 degrees, 25.3+/−0.3 degrees and 5.4+/−0.3 degrees two theta, and optionally further comprising at least one peak selected from 25.8+/−0.3 degrees, 15.9+/−0.3 degrees and 29.9+/−0.3 degrees two theta. In some embodiments, the x-ray powder diffraction pattern further comprises at least one peak selected from 21.6+/−0.3 degrees, 16.5+/−0.3 degrees and degrees two theta. The x-ray powder diffraction pattern may further comprise peaks at 21.3+/−0.3 degrees, 17.1+/−0.3 degrees, 16.3+/−0.3 degrees, 33.1+/−0.3 degrees, 45.6+/−0.3 degrees and 13.7+/−0.3 degrees two theta. In some embodiments, crystalline Form I is characterized by an x-ray powder diffraction pattern substantially as set forth in FIG. 3. Greater than 90%, 95% or 99% by weight of the compound of Formula I in the composition may be crystalline Form I. In some embodiments, the composition comprises 0.01 mg to 200 mg of crystalline Form I, such as about 10 mg, 25 mg, 50 mg, 75 mg, 100 mg or 200 mg of crystalline Form I In some embodiments, a composition comprising crystalline form of PRX-3140 potassium salt comprises 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% PRX-3140 potassium salt (wt/wt) or (w/v) of the composition. In some embodiments, a composition comprising crystalline form of PRX-3140 potassium salt comprises 0.01%, 0.05%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% PRX-3140 potassium salt (wt/wt) or (w/v) of the composition.

The compounds and compositions of the present disclosure can be administered to a subject in need thereof by any route known in the art, including without limitation, oral, parenteral, topical, and intraductal delivery. Accordingly, compositions disclosed herein are formulated to be compatible with the intended route of administration.

In some embodiments, the compositions comprising crystalline form of PRX-3140 potassium salt further comprise an excipient. Such an excipient can be compatible with the intended route of administration.

IV. Methods of Making a Particle Delivery System (PDS)

The present disclosure also provides a method of making a composition of the present disclosure comprising particles of the crystalline form of PRX-3140 potassium salt encapsulated by an excipient, the method comprising:
blending crystalline form of PRX-3140 potassium salt together with an excipient to form a mixture;
processing said mixture to form coarse particles having an average diameter ranging from about 0.1 mm to about 5 mm; and
grinding or milling said coarse particles to form particles having an average diameter less than about 500 micrometers.

In certain embodiments, the particles have an average diameter ranging from about 0.1 microns to about 0.1 mm. Particulate materials, also designated as "particles", to be produced in accordance with this disclosure are those in which small nanometer to micrometer size particles may be desirable. Examples may include nanoparticles and microparticle forms of pharmaceuticals, including crystalline form of PRX-3140 potassium salt. The possibilities and combinations are numerous.

In one embodiment, a system for preparing a composition of the present disclosure may include a grinding the crystalline form of PRX-3140 potassium salt in a mortar and pestle or with a ball mill. In another embodiment a system for preparing a composition of the present disclosure may include a venturi-type nozzle or 'Tee' valve to introduce cryogenic gas to, for example, a jet mill. Without wishing to be bound by any particular theory, combinations of dry gases at cryogenic temperatures (generally below 0 degrees Celsius) before introduction into the jet mill may be used to eliminate moisture-induced agglomeration, as well as promote brittle fracture of particles upon impaction, and has been observed to act synergistically to produce a marked improvement in the particle size reduction efficiency. Cryogenic liquids suitable for use in this method include liquid argon, liquid nitrogen, liquid helium or any other liquified gas having a temperature sufficiently low to produce brittle fracture of particles. The cryogenic liquid may also prevent milling losses and thermal damage to the feed material that would otherwise be caused by the volatization or overheating of constituent ingredients.

In one embodiment, a powder is placed in a temperature-controlled vessel, such as a jacketed hopper or a screw-feeder or is frozen beforehand. The cryogenic liquid and gas inputs are opened, and the flow and temperature are set to the desired process conditions. The cryogenic gas input system, for example liquid nitrogen mixed with nitrogen gas, may be connected to a standard commercial jet mill, such as a Trost Gem-T, Trost T-15, Fluid Air Aljet, Hosikawa Alpine AS Spiral Jet Mill, Sturtevant Micronizer, or similar system, as the main carrier gas in a variety of gas input setups. Pre-run setup of the system may include attaching a temperature probe or flowmeter, such as a TSI Model 4040 Flowmeter or similar system, at the gas input or to the top of the cyclone (in place of air relief bag), setting the carrier gas on different input pressures and documenting the gas flow and temperature measurements (CFM). The milling process may be started by turning on the powder feeder and after passing powder through the milling region, the jet-milled powder is collected in the cup or similar receiver unit (typically particles ~1-10 microns) or from the bag above the cyclone (particles<1 micron), depending on the exact run conditions. Particles with diameters ranging from less than about 1 micron to about microns may be produced by running the powder from the cup through the jet-mill under similar run conditions multiple times, or passes, to obtain the desired particle size.

In certain embodiments, the particles may have an average diameter ranging from about mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns and may be able to pass through a 50-mesh sieve. In certain embodiments, the particles have a diameter of about 0.6 mm or less.

In certain embodiments, the controlled-release polymer is heated prior to blending with the crystalline form of PRX-3140 potassium salt.

In some embodiments, the present disclosure provides a method of making a composition of the present disclosure comprising particles of the crystalline form of PRX-3140 potassium salt encapsulated by a controlled-release polymer using a process wherein the process is at least partially a continuous manufacturing process. The method may comprise:
  blending the crystalline form of PRX-3140 potassium salt together with a controlled-release polymer to form a mixture;
  heating said mixture to a temperature sufficient for extrusion of the mixture;
  extruding said mixture to form coarse particles having an average diameter ranging from about 0.1 mm to about 5 mm;
  cooling said coarse particles; and
  processing (e.g., by milling, grinding, or crushing) said coarse particles to form particles having an average diameter less than about 0.1 mm.

In certain embodiments, the particles may have an average diameter ranging from about 0.1 mm (100 microns) to about 3 mm. For example, the particles may have a diameter of less than about 2.06 mm (corresponding to a 10 mesh sieve), less than about 1.68 mm (corresponding to a 12 mesh sieve), less than about 1.40 mm (corresponding to a 14 mesh sieve), less than about 1.20 mm (corresponding to a 16 mesh sieve), less than about 1.00 mm (corresponding to an 18 mesh sieve), less than about 0.853 mm (corresponding to a 20 mesh sieve), less than about 0.710 mm (corresponding to a 25 mesh sieve), less than about 0.599 mm (corresponding to a 30 mesh sieve), or less than about 0.500 mm (corresponding to a 35 mesh sieve). In some embodiments, the particles may have a diameter of less than about 300 microns and may be able to pass through a 50 mesh sieve. In certain embodiments, the particles may have a diameter of about 0.1 mm or less.

In certain embodiments, the controlled-release polymer may be heated prior to blending with the crystalline form of PRX-3140 potassium salt.

V. Pharmaceutical Compositions (Final Dosage Forms)

The present disclosure further provides pharmaceutical compositions (sometimes referred to as "final dosage forms" or "FDF") comprising compositions according to the present disclosure.

In some embodiments, the pharmaceutical compositions may further comprise at least one excipient (such as, e.g., a controlled-release polymer, surfactant, and/or metal salt), such as a pharmaceutically acceptable excipient. Examples of pharmaceutically acceptable excipients may be, for example, those described in Remington's Pharmaceutical Sciences by E. W. Martin, and include cellulose, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the pharmaceutical compositions also contain pH buffering reagents, and wetting or emulsifying agents.

In some embodiments, the pharmaceutical compositions may be formulated for oral administration. In this embodiment, the pharmaceutical composition may be in the form of, for example, tablets, capsules, or other oral dosage forms. Such oral dosage forms may be prepared by conventional means. The pharmaceutical composition can also be prepared as a liquid, for example as a syrup or a suspension. The liquid can include suspending agents (e.g., sorbitol syrup, cellulose derivatives, or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring, and sweetening agents. Alternatively, the composition can be presented as a dry product for constitution with water or another suitable vehicle.

For buccal and sublingual administration, the composition may take the form of tablets or lozenges according to conventional protocols.

The pharmaceutical composition can also be formulated for rectal administration as a suppository or retention enema, e.g., containing conventional suppository bases such as PEG, cocoa butter, or other glycerides.

In some embodiments, the pharmaceutical compositions described herein provide improved dissolution of the crystalline form of PRX-3140 potassium salt, relative to the unencapsulated crystalline form of PRX-3140 potassium salt, and/or to another dosage form (such as, e.g., a more invasive dosage form). For example, dissolution may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 6, 7, 8, 9, 10, 20, 30, 40, 50, 100, or 1000 fold, as measured by a Vankel tablet dissolution apparatus approved by the United States Pharmacopeia.

In some embodiments, the pharmaceutical compositions described herein provide improved oral bioavailability of the crystalline form of PRX-3140 potassium salt, relative to the unencapsulated crystalline form of PRX-3140 potassium salt, and/or to another dosage form (such as, e.g., a more invasive dosage form). For example, absorption may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are immediate-release formulations. In such embodiments, the pharmaceutical compositions provide a more rapid onset of action of the crystalline form of PRX-3140 potassium salt, relative to the unencapsulated crystalline form of PRX-3140 potassium salt, and/or to another dosage form (such as, e.g., a more invasive dosage form). For example, the onset of action may be shortened by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo pharmacokinetic studies in a preclinical animal model or human clinical evaluation.

In some embodiments, the pharmaceutical compositions described herein are controlled-release formulations. In such embodiments, the pharmaceutical compositions described herein provide a more rapid onset of action of the crystalline form of PRX-3140 potassium salt.

In some embodiments, the pharmaceutical compositions described herein have reduced absorption variability, relative to the unencapsulated insoluble drug, and/or to another dosage form (such as, e.g., a more invasive dosage form).

In some embodiments, the pharmaceutical compositions described herein are associated with improved patient compliance, relative to another pharmaceutical composition comprising the crystalline form of PRX-3140 potassium salt (which may be in another dosage form, such as, e.g., a more invasive dosage form).

In some embodiments, a pharmaceutical composition of the present disclosure is formulated for oral delivery. Compositions intended for oral use may be prepared in solid or fluid unit dosage forms. In at least some embodiments, the compositions are formulated for oral delivery as tablets, caplets, capsules, pills, powders, troches, elixirs, suspensions, syrups, wafers, chewing gums, dragees, lozenges, and the like.

In some embodiments, the oral dosage forms are solid oral dosage forms such as tablets, caplets, and capsules. In some embodiments, the capsule is a hard capsule or a soft capsule. In other embodiments, the capsule is a gelatin capsule, gelatin-free capsule, a "cap-in-cap" capsule, alginate capsule, hydroxypropylmethyl cellulose (HPMC) capsule, a polyvinyl alcohol (PVA) capsule, a hypromellose capsule, or a starch capsule.

In some embodiments, an oral composition comprising the crystalline form of PRX-3140 potassium salt thereof further comprises one or more excipients. In some embodiments, an oral composition comprising the crystalline form of PRX-3140 potassium salt or a polymorph thereof further comprises one or more excipients. Accordingly, compositions designed for oral administration can be made with an inert or active excipient or with an edible carrier as disclosed herein.

In various embodiments, the composition provided herein comprises from about 1% to about 99.99%, about 5% to about 95%, about 5% to about 90%, about 10% to about 80%, about 15% to about 70%, about 20% to about 60%, from about 30% to about 95%, from about 50% to about 90%, from about 60% to about 90%, from about 60% to about 80%, or from about 70% to about 80% by weight of one or more excipients. In certain embodiments, the composition provided herein comprises about 99.99%, about 95%, about 90%, about 85%, about 80%, about 75%, about 70%, about 65%, about 60%, about 55%, or about 50% by weight of one or more excipients. In certain embodiments, the composition provided herein comprises about 99.99%, about 99%, about 98%, about 97%, about 96%, about 95%, about 94%, about 93%, about 92%, about 91%, about 90%, about 89%, about 88%, about 87%, about 86%, or about 85% by weight of one or more excipients. In certain embodiments, the composition provided herein comprises about 85%, about 84%, about 83%, about 82%, about 80%, about 79%, about 78%, about 77%, about 76%, about 75%, about 74%, about 73%, about 72%, about 71%, about 70%, about 69%, about 68%, about 67%, about 66%, or about 65% by weight of one or more excipients. In certain embodiments, the composition provided herein comprises about 55%, about 54%, about 53%, about 52%, about 51%, about 50%, about 49%, about 48%, about 47%, about 46%, or about 45% by weight of one or more excipients. In certain embodiments, the composition provided herein comprises about 30%, about 29%, about 28%, about 27%, about 26%, about 25%, about 24%, about 23%, about 22%, about 21%, or about 20% by weight of one or more excipients.

Examples of excipients that can be used in the compositions formulated for oral administration are provided herein and can include, but are not limited to, one or more of bulking agents, binders, fillers, disintegrating agents, lubricants, glidants, control release agents, enteric coatings, film-forming agents, plasticizers, colorants, sweetners, flavoring agents and the like, or any combination thereof.

Binders suitable for use in the pharmaceutical compositions provided herein include, but are not limited to, sucrose, starches such as corn starch, potato starch, or starches such as starch paste, pregelatinized starch, and starch 1500, PEG 6000, methocel, walocel HM, Luvitec, Luvicaparolactam, Avicel, SMCC, UNIPURE, gelatin, natural and synthetic gums such as acacia, sodium alginate, alginic acid, other alginates, tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, polyvinyl pyrrolidone, hydroxypropyl methyl cellulose, (e.g., Nos 2208, 2906, 2910), microcrystalline cellulose, and mixtures thereof. Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. In some embodiments, the binder is a mixture of microcrystalline cellulose and sodium carboxymethyl cellulose. Suitable anhydrous or low moisture excipients or additives include AVICEL PH 103 and Starch 1500 LM.

Examples of fillers suitable for use in the pharmaceutical compositions provided herein include, but are not limited to, talc, calcium carbonate (e.g., granules or powder), sugars such as dextrose, sucrose, lactose, a salt such as calcium carbonate, calcium phosphate, sodium carbonate, sodium phosphate, starches, microcrystalline cellulose, powdered cellulose, cellulosic bases such as methyl cellulose, carboxymethyl cellulose dextrates, kaolin, mannitol, silicic acid, sorbitol, starch, pregelatinized starch, and mixtures thereof.

One or more binder or filler in compositions is typically present in from about 10% to about 99% (wt/wt) of the composition or the dosage form. In some embodiments, binders and/or fillers in a composition comprise about 15% to 99%, about 20% to 60%, about 25% to 55%, about 30% to 50%, about 35% to 60%, about 50% to 99% (wt/wt) of the composition.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. In some embodiments, the disintegrant is deep in the oral solid dosage form to delay disintegration. The amount of disintegrant used varies based upon the type of formulation, and is readily discernible to those of ordinary skill in the art.

Typical compositions comprise from 0.5% to 15% (wt/wt) of disintegrant. In some embodiments, compositions comprise from 1% to 5% (wt/wt) of disintegrant in the composition. In another embodiment, the disintegrant is 1% to 25%, 2% to 20%, 5% to 15%, 8% to 12%, or about 10% (wt/wt) of the composition.

Disintegrants that can be used in the pharmaceutical compositions provided herein include, but are not limited to, agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, magnesium stearate or potassium stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), Q7-9120 (Dow Corning), and mixtures thereof. If used at all, lubricants are typically used in an amount of less than 1% (wt/wt) of the compositions or dosage forms into which they are incorporated. In yet another embodiment, the lubricant is 0.1% to 3%, such as 0.5% to 1% (wt/wt), of the composition.

Plasticizers may be added to control the softness or pliability of oral dosage forms such as shell of a capsule, caplet or a tablet and thus, may improve the mechanical properties of the pH-sensitive materials of the coatings on the oral dosage forms. Suitable plasticizers, include, without limitation, petroleum oils (for e.g., a paraffinic process oil, a naphthenic process oil, and an aromatic process oil), squalene, squalane, plant oils, (e.g., olive oil, camelia oil, castor oil, tall oil, and a peanut oil), silicon oils, dibasic acid esters, (e.g., dibutyl phthalate, and dioctyl phthalate), liquid rubbers (e.g., polybutene and a liquid isoprene rubber), liquid fatty acid esters (e.g., isopropyl myristate ISM), hexyl laurate, diethyl sebacate, and diisopropyl sebacate, triethyl citrate, triacetin, diethylene glycol, polyethylene glycols, polypropylene glycol, phthalates, sorbitol, glycol salicylate, crotaminton, and glycerin or mixtures thereof. The amount of plasticizer may vary depending upon the chemical composition of the pharmaceutical preparation. In one embodiment, the at least one plasticizer is sorbitol, dimethyl isosorbide, or a glycerol. In another embodiment, the plasticizer is 1% to 10%, such as 3% to 5% (wt/wt), of the composition.

Examples of glidants include, but are not limited to, colloidal silicone dioxide, cellulose, calcium phosphate, di or tri-basic and the like.

As an example of sweeteners or sweetening agents include sucrose, saccharin, dextrose, maltose, sugar substitutes, aspartame, xylitol, mannitol, cyclamate, sucralose, maltitol, sorbitol, acesulfame K and the like.

Examples of flavoring agents include peppermint, methyl salicylate, peppermint, spearmint, methyl salicylate, raspberry, red berry, strawberry, pineapple, orange, cherry and the like.

Compositions formulated for oral delivery as disclosed herein, for example, tablets, caplets, and capsules, may be coated with one or more enteric coating agent, control release agent or film forming agent to control or delay disintegration and absorption of the compositions comprising the crystalline form of the compound of Formula I thereof in the gastrointestinal tract and thereby provide a sustained action over a longer period of time. Accordingly, in some embodiments, the tablet can be an enteric tablet, the caplet can be an enteric caplet, or the capsule can be an enteric capsule. The enteric tablets, enteric caplets, or enteric capsules of the present disclosure may be prepared by techniques known in the art.

Pharmaceutical preparations disclosed herein may comprise a control release agent. Examples of control release agent suitable for use include, without limitation, pH-dependent polymers, acid-insoluble polymers, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, waxes, including synthetic waxes, microcrystalline waxes, paraffin wax, carnauba wax, and beeswax; polyethoxylated castor oil derivatives, hydrogenated oils, glyceryl mono-, di-tribenates, glyceryl monostearate, glyceryl distearate, long chain alcohols, such as stearyl alcohol, cetyl alcohol, and polyethylene glycol; and mixtures thereof. In some embodiments, a time delay material such as glyceryl monostearate or glyceryl distearate may be used. In other embodiments, the controlled release reagent is a digestible waxy substance such as hard paraffin wax.

In some embodiments, compositions may comprise one or more of pH-dependent polymers such as acid insoluble polymers. The pH-dependent polymers become increasingly permeable above pH 5.0 but are impermeable at pH below 5.0 whereas acid insoluble polymers become soluble in neutral to weakly alkaline conditions. Such control release polymers target upper small intestines and colon. Non-limiting examples of acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (commercially available under the tradename EUDRAGIT(R) L and EUDRAGIT(R) S from Rohm America In, Piscataway, N.J. as a powder or a 30% aqueous dispersion; or under the tradename EAST-ACRYL(R), from Eastman Chemical Co., Kingsport, Tenn., as a 30% dispersion). Additional examples include EUDRAGIT(R) L100-55, EUDRAGIT(R) L30D-55, EUDRAGIT(R) L100, EUDRAGIT(R) L100 12,5, EUDRAGIT(R) S100, EUDRAGIT(R) S12,5, EUDRAGIT (R) FS 30D, EUDRAGIT(R) E100, EUDRAGIT(R) E 12,5, and EUDRAGIT(R) PO. In at least one embodiment, the composition comprises EUDRAGIT(R) L100-55. EUDRAGIT(R) RS and RL and EUDRAGIT(R) NE and NM are also useful polymers for the purpose of this disclosure. In some embodiments, the composition comprises EUDRAGIT(R) L30D 55. In another embodiment, the preparation comprises EUDRAGIT(R) FS 30D. One of skill in the art will recognize that at least some acid insoluble polymers listed herein will also be biodegradable.

For time delay or delayed-release pharmaceutical preparations of oral dosage forms, glyceryl monostearate, glyceryl distearate, and acid-insoluble polymers, for example polymethacrylate pH-sensitive polymer-based coatings can be used, (e.g., as coating material, i.e., enteric coating agents, for enteric coating of capsules, caplets, and tablets). Commercial sources for delayed-release oral dosage forms are available, for example DRCaps made of hypromellose (HPMC) from Capsugel, USA. Such delayed-release oral dosage forms are acid-resistant and can resist acidity as seen in stomach for at least 30 min, such as for at least 1 hour, for at least 1.5 hour, or for at least 2 hours. Such delayed release oral dosage forms can release at least 40%, at least 50%, at least 60%, at least 70%, at least 80% or at least 90% of the crystalline form of the compound of Formula I thereof in the intestines (small intestines, large intestine/colon etc).

In an aspect of the present disclosure, the enteric tablets, enteric caplets, and enteric capsules may be uncoated. Hard uncoated capsules with enteric capability using intrinsically enteric capsule technology (for example, EnTrinsic Drug Delivery available from Capsugel) are suitable for the purpose of the present disclosure.

In various embodiments, the enteric tablet is a hard tablet made with free-flowing powder of the crystalline form of the compound of Formula I thereof. In various embodiments, the enteric capsule is a capsule made with free-flowing powder of crystalline form of the the compound of Formula I thereof. In various embodiments, the enteric tablet is a hard tablet made with free-flowing powder of the crystalline form of the compound of Formula I. In various embodiments, the enteric capsule is a capsule made with free-flowing powder of the crystalline form of the compound of Formula I.

In some embodiments, the enteric capsule is a non-animal-based capsule, such as a hypromellose capsule (for example, commercially available self-gelling Vcaps, VCaps Plus, VCaps enteric, other enteric capsules made using Xcellodose, ENCODE colonic delivery technology, and EnTrinsic™. drug delivery technology from Capsugel). Other technologies known in the art and available commercially (for example, Qualicaps, USA, Nutrascience, USA, etc.) for the formulating enteric forms of oral solid dosage forms can also be utilized. In at least one embodiment, the capsule is an API-in-capsule, meaning that the crystalline form of the compound of Formula I free base or salts thereof is filled neat into the capsule. In such API-in-capsule oral dosage forms, the active ingredient, the crystalline form of the compound of Formula I can be free flowing powders or micronized powders. When the dosage Form I is a capsule, in at least one embodiment, the capsule can be a seamless capsule or a banded capsule.

Dissolution of the oral dosage forms disclosed herein is tested by the dissolution tests according to the current methods of USP 711. In some embodiments, the oral dosage forms disclosed herein are protected from the acidic environment of the stomach and do not dissolve for at least 2 hours, at least 3 hours, at least 4 hours, at least 5 hours, 6 hours, at least 7 hours or at least 8 hours. In at least one embodiment, the oral dosage forms do not release PRX-3140 for at least 6 hours. In another embodiment, the oral dosage forms do not release PRX-3140 for at least 2 hours.

VI. Methods of Making Pharmaceutical Compositions

In further embodiments, the present disclosure provides a method of making a pharmaceutical composition wherein the method further comprises formulating the particles.

In certain embodiments, the particles are formulated into unit doses such as tablets or capsules.

In some embodiments wherein the pharmaceutical compositions further comprises at least one excipient, the present disclosure also provides a method of making a pharmaceutical composition wherein the method further comprises mixing the particles with at least one excipient to form a second mixture; and formulating the second mixture.

In certain embodiments, the particles are formulated into unit doses such as tablets or capsules.

VII. Methods of Treatment

The pharmaceutical compositions described herein may be useful to treat any disease or condition for which administration of a corresponding insoluble drug is desirable. For example, compositions comprising crystalline form of the compound of Formula I may be useful for the treatment of Alzheimer's disease (AD) and other dementias affecting the cholinergic and/or serotonergic systems including post-traumatic stress disorder (PTSD). The terms "treat," "treatment," and "treating" refer to (1) a reduction in severity or duration of a disease or condition, (2) the amelioration of one or more symptoms associated with a disease or condition without necessarily curing the disease or condition. In some embodiments, the method of treatment further comprises the prevention of a disease or condition. Suitable subjects include, e.g., humans and other mammals, such as, e.g., mice, rats, dogs, and non-human primates.

In yet another aspect, the disclosure provides a method of treating Alzheimer's disease (AD) and other dementias affecting the cholinergic and/or serotonergic systems including post-traumatic stress disorder (PTSD), comprising administering an effective amount of a pharmaceutical composition of the present disclosure to a patient in need thereof.

Other embodiments of the present disclosure will be apparent to those skilled in the art from consideration of the specification and practice of the present disclosure disclosed herein. It is intended that the specification and examples be considered as exemplary only, with the true scope and spirit of the present disclosure.

EXAMPLES

Figure 2:
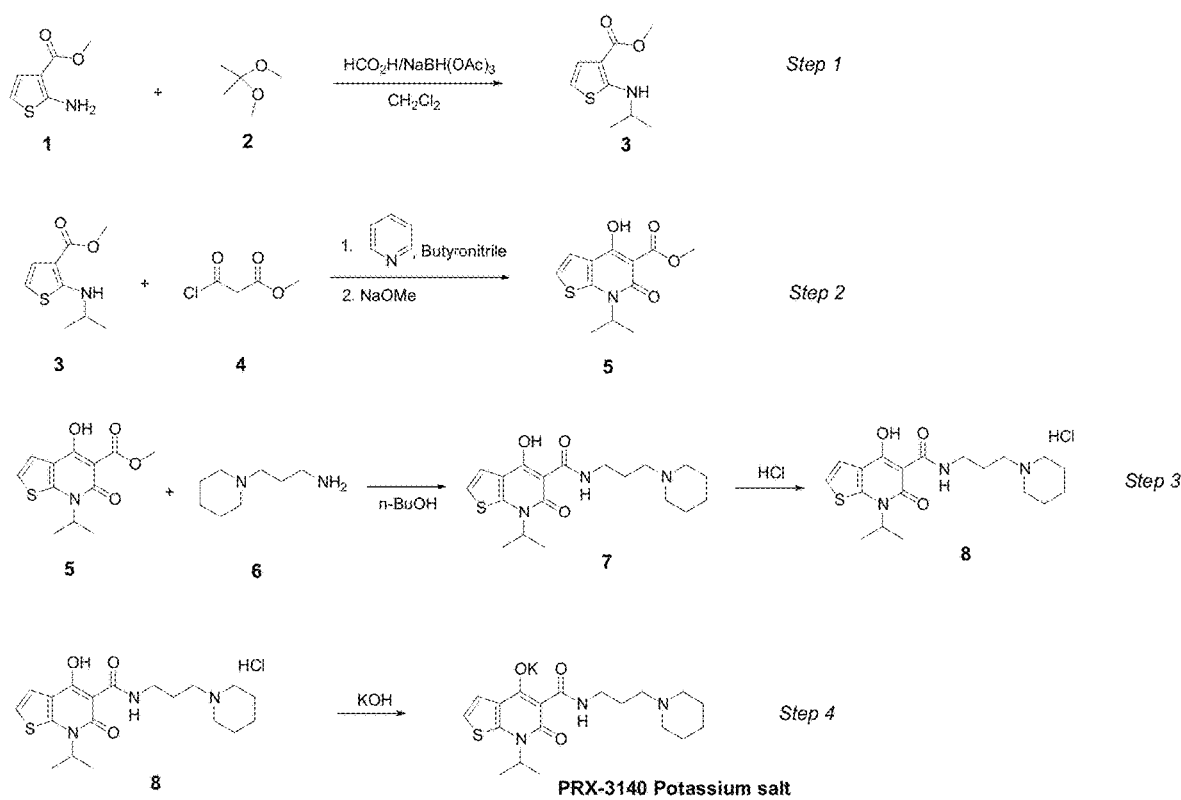
FIG. 2 shows the synthesis of crystalline fine particle Form I of PRX-3140 potassium salt.

Example 1—Small-Scale Preparation of 50 Grams of Crystalline PRX-3140 Potassium Salt U.S. Pat. Nos. 7,488,736 and 7,982,040 described PRX-3140 preparation in a six-step process. Supply of 3-piperidin-1-yl-propylamine allows synthesis of crystalline fine particle Form I of PRX-3140 potassium salt in four-step process at the 50-gram scale as shown in FIG. 2.

Step 1. Reductive amination—Methyl 2-iso-propylaminothiophene-3-carboxylate (3). To a 3 L three-neck round-bottom flask equipped with a mechanical stirrer was added methyl 2-aminothiophene-3-carboxylate (90.52 g, 0.5758 mol) and sodium triacetoxyborohydride (207.48 grams, 0.979 mole). Anhydrous dichloromethane (640 mL) was added and the mixture was stirred for 2 minutes prior to the addition of a solution of formic acid (53.01 grams, 1.1517 mole) and 2,2-dimeoxypropane (299.88 grams, 2.8793 mole) over 30 minutes at 15-32 degrees Celsius (internal temperature) under argon (cooled with cold water if needed). The addition funnel was rinsed with anhydrous dichloromethane (92 mL) and charged to the reaction mixture. After the addition was completed, the resulting mixture was stirred at 25-30 degrees Celsius for 2 hours. The reaction mixture was added to an aqueous solution of potassium hydroxide (304.1 gram, 4.607 mole) in water (905 mL) at 5 degrees Celsius and maintaining the temperature below 40 degrees Celsius Dichloromethane (100 mL) was used to rinse the reaction flask and added to the mixture. The resulting mixture was stirred at room temperature for 0.5 hour, then filtered, and the residue was washed with dichloromethane (300 mL). The filtrate was diluted with water (0.5 L), and the phases were separated. The aqueous phase was extracted with dichloromethane (0.5 L). The combined organic phase was mixed with water (0.5 L) and stirred for 0.5 hour. The phases were separated again, and the organic phase was dried over $Na_2SO_4$. Filtration and concentration provided 114.7 grams crude as red oil, which was dissolved in heptane (0.50 L) and stirred with neutral alumina (90 grams) for 0.5 hour, then filtered, and the filtrate was evaporated. The titled compound (105.8 g, 92%) was obtained as yellowish oil. HPLC purity: 98.2%. 1H NMR (300 MHz, $CDCl_3$) δ 7.35 (br s, 1 H), 7.00 (d, J=5.7 Hz, 1H), 6.14 (dd, J=5.7, 1.2 Hz, 1H), 3.78 (s, 3H), 3.56-3.44 (m, 1H), 1.32 (s, 3H), 1.29 (s, 3H).

Step 2. Acylation and cyclization—Methyl 4-hydroxy-7-isopropyl-6-oxo-6,7-dihydro-thieno[2,3-b]pyridine-5-carboxylate (5). To a solution of starting amine 3 (89.7 grams, 0.450 mole) and pyridine (71.2 grams, 0.900 mole) in butyronitrile (0.9 L) was heated to 70-75 degrees Celsius with stirring under argon. A solution of methyl malonyl chloride (116.7 grams, 0.855 mol) in butyronitrile (0.45 L) was added drop-wise to the reaction mixture to maintain the temperature at 70-75 degrees Celsius (internal temperature) with vigorous stirring (with occasional turn off of the heating, especially in the beginning). At the end of addition, the temperature was held for 8 to 10 minutes before sodium methoxide solution (25%, 390.0 grams, 415 mL, 1.80 mol) was added over 10 minutes at the same temperature. The resulting mixture was stirred at the same temperature for 10 minutes, then cooled to room temperature. Water (0.45 L) was added, and the mixture was stirred for 20 minutes at room temperature. The phases were separated, and the organic phase was extracted with water (0.45 L). The combined aqueous phase was washed with EtOAc (2×0.45 L). The aqueous phase was then acidified to pH 4.0-4.5 with 1:5 v/v HCl/water at room temperature. The resulting solid was filtered and washed with water (2×180 mL). The filter cake was dried on vacuum oven at 45-50 degrees Celsius overnight. Title compound was obtained (68.48 g, 57%) as yellow solid. HPLC purity: 98.1%. The filtrate was cloudy overnight and 2nd filtration provided 2nd crop (9.68 g, 8%, HPLC purity: 87.4%), which was not used for next step. 1H NMR (300 MHz, CDCl3) δ 7.32 (d, J=5.7 Hz, 1H), 6.90 (d, J=6.0 Hz, 1H), 4.00 (s, 3H), 1.70-1.60 (m, 1H), 1.64 (s, 3H), 1.61 (s, 3H).

Step 3. Amidation and salt formation 4-Hydroxy-7-isopropyl-6-oxo-6,7-dihydro-thieno[2,3-b]pyridine-5-carboxylic acid (3-piperidin-1-yl-propyl)-amide hydrochloride (8). A mixture of methyl 4-hydroxy-7-isopropyl-6-oxo-6,7-dihydro-thieno[2,3-b]pyridine-5-carboxylate (5, 2 grams, 7.48 mmol) and 3-piperidin-1-yl-propylamine (6, 1.12 g, 7.85 mmol, 1.05 equiv.) was heated at 90-95 degrees Celsius for 2 hours. TLC analysis indicated that the reaction was complete. The reaction mixture was cooled to room temperature, diluted with water (5 mL), and charged with 1M HCl (7.4 mL). The organic layer was separated and washed with water (4 mL). The organic layer was treated with concentrated hydrochloric acid (1.4 grams). The organic phase was concentrated to ca. 11 mL (9.9 grams). The residue was charged with n-butanol (10 mL). The mixture was re-concentrated to a volume of ca. 11 mL (9.9 grams). The residue was heated to 50 degrees Celsius and diluted with MTBE (20 mL). The mixture was stirred at 50 degrees Celsius for 40 minutes, cooled to room temperature, and then held at −10 degrees Celsius overnight. The slurry was filtered at 0-5 degrees Celsius. The filter cake was washed with n-butanol/MTBE (1:3, 2×4 mL) and dried on rotavapor to give 4-hydroxy-7-isopropyl-6-oxo-6,7-dihydro-thieno[2,3-b]pyridine-5-carboxylic acid (3-piperidin-1-yl-propyl)-amide hydrochloride (8, 2.35 grams, yield: 75%, HPLC: 99.65%) as a white solid. The batch started with 66.35 g of ester 5 and 84.5 g of title compound 8 was obtained (yield: 82%). 1H NMR (300 MHz, DMSO-$d_6$) δ 10.24 (br t, J=5.4 Hz, 1H), 9.91 (br s, 1 H), 7.38 (d, J=5.7 Hz, 1H), 7.32 (d, J=5.7 Hz, 1H), 3.47-3.30 (m, 4H), 3.08-2.98 (m, 2H), 2.90-2.76 (m, 2H), 2.05-1.93 (m, 2H), 1.82-1.62 (m, 6H), 1.57 (s, 3H), 1.55 (s, 3H), 1.44-1.26 (m, 1H).

Step 4: Preparation of 4-Hydroxy-7-isopropyl-6-oxo-6,7-dihydro-thieno[2,3-b]pyridine-5-carboxylic acid (3-piperidin-1-yl-propyl)-amide potassium salt (PRX-3140 potassium salt). A mixture of 4-hydroxy-7-isopropyl-6-oxo-6,7-dihydro-thieno[2,3-b]pyridine-5-carboxylic acid (3-piperidin-1-yl-propyl)-amide hydrochloride (8, 2.35 g, 5.68 mmol), MTBE (23.5 mL), water (11.75 mL) and 1M KOH solution (5.6 mL) was stirred at room temperature for 20 minutes. The mixture still had insoluble hydrochloride salt. $NaHCO_3$ (0.49 gram) was added to above mixture and continued to stir for 0.5 hour. The mixture became a clear solution. The organic layer was separated. The aqueous layer was extracted with additional MTBE (20 mL). The combined organic layers were concentrated to dryness to give 4-hydroxy-7-isopropyl-6-oxo-6,7-dihydro-thieno[2,3-b]pyridine-5-carboxylic acid (3-piperidin-1-yl-propyl)-amide (2.17 grams) as free base.

The above free base (2.17 gram, 5.68 mmol) was dissolved in acetonitrile (23.5 mL) at degrees Celsius To above solution was added a solution of KOH (0.43 gram, 6.53 mmol) in water (1.8 mL). The resulting mixture was stirred at 50 degrees Celsius for 0.5 hours, cooled to room temperature, then cooled at 0-5 degrees Celsius for 3 hours. The solid was filtered to give 3 grams of wet product which was dissolved into a mixture of acetonitrile (42 mL) and water (3 mL) at 50 degrees Celsius. The solution was filtered to remove insoluble solid. The filtrates were concentrated to a volume of 21 mL. Acetonitrile (21 mL) was added and concentrated to a volume of 21 mL. This process repeated twice. The residue was placed in ice-water bath for 3 hours, filtered and the filter cake was washed with acetonitrile (at 0 degrees Celsius, 2×6 mL), dried on rotavapor to give crystalline 4-hydroxy-7-isopropyl-6-oxo-6,7-dihydro-thieno[2,3-b]pyridine-5-carboxylic acid (3-piperidin-1-yl-propyl)-amide potassium salt (1.75 gram, yield: 74.2%; HPLC: 99.9%, KF: 1.19%) as white solid. The batch started with 84.5 grams of hydrochloride salt 8 converted to 76.3 grams of crystalline fine particle Form I of PRX-3140 potassium salt (yield: 90%; HPLC: 99.6%, KF: 0.66%). 1H NMR (300

MHz, DMSO-d$_6$) δ (t, J=5.3 Hz, 1H), 7.13 (d, J=5.4 Hz, 1H), 6.80 (d, J=5.4 Hz, 1H), 3.19-3.11 (m, 2H), 2.70-2.40 (m, 6H), 1.62-1.30 (m, 15H).

Example 2—X-ray Diffraction of Crystalline PRX-3140 Potassium Salt Prepared at Two Scales Crystalline fine particle Form I of PRX-3140 potassium salt samples of Examples 1 and a scale-up batch were used to identify differences in the crystalline structure of the two samples through standard x-ray diffraction (XRD) measurement. In both examples the same peaks were obtained shown in FIGS. 3 and 4 as well as Tables 1 and 2, respectively.

TABLE 1

XRD of Example 1 crystalline fine particle Form I of PRX-3140 potassium salt

| Peak Value (degree) | Peak Intensity | Peak Value (degree) | Peak Intensity |
| --- | --- | --- | --- |
| 5.441 | 1087 | 40.050 | 283 |
| 11.875 | 457 | 40.651 | 160 |
| 12.994 | 304 | 41.069 | 308 |
| 13.730 | 460 | 41.738 | 204 |
| 15.919 | 696 | 42.456 | 314 |
| 16.286 | 501 | 43.225 | 209 |
| 16.520 | 553 | 43.793 | 280 |
| 17.089 | 509 | 44.746 | 327 |
| 19.428 | 254 | 44.930 | 339 |
| 19.879 | 172 | 45.297 | 391 |
| 20.331 | 536 | 45.581 | 474 |
| 20.648 | 160 | 46.283 | 252 |
| 21.266 | 524 | 46.751 | 160 |
| 21.601 | 566 | 46.985 | 173 |
| 22.303 | 1935 | 48.222 | 243 |
| 22.938 | 419 | 48.773 | 181 |
| 23.556 | 314 | 48.924 | 164 |
| 24.325 | 444 | 49.308 | 176 |
| 24.726 | 365 | 49.676 | 165 |
| 25.260 | 1325 | 50.578 | 228 |
| 25.829 | 930 | 52.617 | 190 |
| 26.347 | 163 | 53.937 | 172 |
| 27.433 | 441 | 54.355 | 175 |
| 28.553 | 237 | 54.806 | 169 |
| 29.137 | 212 | 56.059 | 160 |
| 29.923 | 619 | 58.048 | 161 |
| 30.792 | 165 | | |
| 32.613 | 306 | | |
| 33.081 | 481 | | |
| 34.435 | 382 | | |
| 34.853 | 223 | | |
| 35.789 | 246 | | |
| 36.440 | 274 | | |
| 36.891 | 172 | | |
| 37.276 | 212 | | |
| 39.264 | 321 | | |
| 39.649 | 228 | | |

TABLE 2

XRD of Scale-up batch of crystalline fine particle Form I of PRX-3140 potassium salt

| Peak Value (degree) | Peak Intensity | Peak Value (degree) | Peak Intensity |
| --- | --- | --- | --- |
| 5.444 | 233 | 41.624 | 163 |
| 11.928 | 228 | 41.824 | 186 |
| 13.031 | 162 | 42.526 | 294 |
| 13.783 | 245 | 43.144 | 171 |
| 15.989 | 431 | 43.295 | 197 |
| 16.356 | 298 | 43.796 | 213 |
| 16.574 | 324 | 43.947 | 220 |
| 17.142 | 294 | 44.849 | 298 |
| 19.498 | 203 | 45.668 | 369 |
| 20.400 | 321 | 46.303 | 217 |
| 21.336 | 371 | 46.955 | 192 |
| 21.654 | 374 | 48.342 | 240 |
| 22.389 | 1222 | 49.027 | 167 |
| 23.007 | 280 | 49.361 | 196 |
| 23.609 | 247 | 49.762 | 160 |
| 24.378 | 342 | 49.929 | 160 |
| 24.812 | 295 | 50.648 | 205 |
| 25.330 | 810 | 50.965 | 160 |
| 25.898 | 637 | 51.818 | 161 |
| 26.734 | 161 | 52.737 | 165 |
| 27.486 | 264 | 53.957 | 160 |
| 28.622 | 203 | 54.241 | 160 |
| 29.207 | 191 | 54.408 | 160 |
| 29.993 | 394 | 54.892 | 204 |
| 30.611 | 241 | 56.079 | 160 |
| 32.683 | 215 | 58.836 | 160 |
| 33.151 | 338 | | |
| 34.438 | 269 | | |
| 35.507 | 160 | | |
| 35.842 | 189 | | |
| 36.159 | 160 | | |
| 36.527 | 206 | | |
| 37.312 | 200 | | |
| 38.432 | 161 | | |
| 39.368 | 320 | | |
| 40.136 | 232 | | |
| 41.173 | 247 | | |

Example 3—PRX-3140 Potassium Salt Photostability Study

Two samples of crystalline fine particle Form I of PRX-3140 potassium salt were prepared for photostability testing: (1) 1.5 grams spread evenly across a glass Petri dish and covered with a transparent quartz cover and (2) 1.5 grams spread evenly across a glass Petri dish and covered with aluminum foil. Samples were exposed to ICH photostability guideline Q1B=1.2 million lux hours of cool, white fluorescent light & 200 watt hours/m2 of UVA light at 40 degrees Celsius/75% RH. Samples were exposed for 2 days and tested using HPLC The control photostability sample of PRX-3140 potassium salt met the specification and showed HPLC results comparable to those obtained for the t=0 sample although an increase in water content from 0.9% w/w to 3.1% w/w was observed. The light exposure was performed in a cabinet set at 25 degrees Celsius/60% RH. The sample was notably lumpy and required grinding to obtain precise assay results.

TABLE 3

| Photostability Study Appearance | t = 0 Light brown solid | Control Pinkish solid | Exposed Sample Orange |
| --- | --- | --- | --- |
| Water Content - KF | 0.9% w/w | 3.1% w/w | 4.3% w/w |
| Total impurities | 0.22% | 0.20% | 0.77% |
| Unknown (RRT 0.55) | 0.01% | 0.01% | 0.01% |
| Unknown (RRT 0.74) | 0.01% | 0.01% | 0.02% |
| Unknown (RRT 0.75) | 0.01% | 0.01% | 0.01% |
| Unknown (RRT 0.86) | nd | nd | 0.01% |
| Unknown (RRT 0.87) | 0.09% | 0.09% | 0.10% |
| Unknown (RRT 0.90) | nd | nd | 0.01% |
| Unknown (RRT 0.91) | nd | nd | 0.01% |

TABLE 3-continued

| Photostability Study Appearance Water Content - KF | t = 0 Light brown solid 0.9% w/w | Control Pinkish solid 3.1% w/w | Exposed Sample Orange 4.3% w/w |
|---|---|---|---|
| Unknown (RRT 0.95) | 0.05% | 0.04% | 0.05% |
| Unknown (RRT 0.98) | 0.01% | 0.01% | 0.04% |
| Unknown (RRT 1.07) | nd | 0.01% | 0.06% |
| Unknown (RRT 1.12) | 0.01% | 0.01% | 0.02% |
| Unknown (RRT 1.22) | 0.01% | 0.01% | 0.01% |
| Unknown (RRT 1.50) | nd | nd | 0.02% |
| Unknown (RRT 1.54) | nd | nd | 0.01% |
| Unknown (RRT 1.57) | nd | nd | 0.01% |
| Unknown (RRT 1.63) | nd | nd | 0.05% |
| Unknown (RRT 1.72) | nd | nd | 0.04% |
| Unknown (RRT 1.72) | nd | nd | 0.02% |
| Unknown (RRT 1.75) | nd | nd | 0.04% |
| Unknown (RRT 1.76) | nd | nd | 0.03% |
| Unknown (RRT 1.79) | nd | nd | 0.01% |
| Unknown (RRT 1.83) | nd | nd | 0.16% |
| Unknown (RRT 2.01) | 0.01% | nd | nd |
| Unknown (RRT 2.06) | nd | nd | 0.01% |
| Unknown (RRT 2.08) | nd | nd | 0.01% |
| Unknown (RRT 2.16) | 0.01% | nd | 0.01% |
| Unknown (RRT 2.38) | 0.01% | nd | nd |

Key to table
RRT = Relative Retention Time, nd = not detected

FIG. 4 shows the PRX-3140 potassium salt photostability study HPLC chromatograms (A) unexposed control sample and (B) PRX-3140 potassium salt photostability exposed sample. Changes were evident for crystalline fine particle Form I of PRX-3140 potassium salt after exposure to UVA and white light. The sample changed color particularly on the upper exposed surface of the material and there were changes apparent in the HPLC data. The illuminated photostability sample of PRX-3140 potassium salt met the USP stability specification of (1) total impurities not more than 2.0% area and (2) no single impurity greater than 0.5% area with a reported assay value of 94.2% w/w, which was below the specification limit. The single impurity profile met the specification (<0.2%) but significant changes were observed. There was an increase in the number of minor impurities, particularly in a region of the chromatogram between RRT 1.5 and 2.1. Total impurities increased from 0.20% in the control sample to 0.77% in the exposed sample. An impurity at RRT 1.83 which was not present before exposure to light was formed at 0.16% in the exposed sample. Other changes included a change in appearance of the material to a sticky solid and an increase in water content to 4.3% w/w.

Example 4—Crystalline PRX-3140 Potassium Salt Forced Degradation Study

Crystalline fine particle Form I of PRX-3140 potassium salt was subjected to a forced degradation study using acid, base, or hydrogen peroxide exposure for 24 hours. Samples were neutralized and analyzed using LC-UV-MS. Table 4 lists the LC-UV-MS conditions.

TABLE 4

| LC-UV-MS conditions | |
|---|---|
| HPLC/MS | Agilent LC/MSD 6120B |
| Source | Electrospray (ESI) |
| Method | Gradient |
| Diluent | 20/80 Methanol/Water |
| Mobile Phase A | Water with 0.1% Formic Acid |
| Mobile Phase B | Acetonitrile with 0.1% Formic Acid |

TABLE 4-continued

| LC-UV-MS conditions | |
|---|---|
| Gradient | 90/10 A/B -> 90/10 A/B (1 min) -> 40/60 A/B (20 min) -> 10/90 A/B (30 min) -> 10/90 A/B (35 min) -> 90/10 A/B (35.5 min) -> 90/10 A/B (40 min) |
| Column | Waters Atlantis T3, 3 µm, 150 × 4.6 mm |
| Temp | 30 degrees Celsius |
| Flow Rate | 1 mL/min |
| Injection Volume | 10 µL |
| UV Detection | 250, 220, and 320 nm |
| Scan | 125 to 1000 m/z |
| Step Size | 0.1 m/z |
| Fragmentor | 150 V |
| Gain | 5 |
| Threshold | 100 |
| Drying Gas | 325 degrees Celsius |
| Capillary | 3000 V |
| Nebulizer Gas | 7 LPM |

Control Sample: FIG. 6A is HPLC UV chromatogram of the crystalline fine particle Form I of PRX-3140 potassium salt Standard (Control) at 250 nm. The UV spectra for the parent molecule is shown in FIG. 6B. Maximums are noted at 220, 250, and 320 nm. Chromatograms for all samples were collected at all three wavelengths with 250 nm being the primary wavelength based on lambda max. The starting material was 98.6% pure based on peak area at 250 nm. The mass spectra at 12.2 minutes for the parent molecule, PRX-3140, is shown in FIG. 6C. The protonated PRX-3140 molecular ion, [M+H]+, is noted at 378.2 m/z.

Sample Preparation: Crystalline fine particle Form I of PRX-3140 potassium salt, 50 mg, was weighed out into a 25 mL volumetric flask and taken to volume with water (2 mg/mL stock). One mL of stock was added to four, 4 mL vials. One mL of either 1N HCl, 1N NaOH, 3% H2O2, or DI Water (control) was added to the appropriate vial, mixed, and stored at room temperature for 24 hours. After storage, the samples of acid and base were neutralized by addition of 1 mL their counter solution. One mL of water was added to the peroxide sample and the control so that all samples had a final concentration of 0.67 mg/mL. Samples were analyzed using LC-UV-MS.

Table 5 lists a comparison for the control, acid, base, and peroxide samples showing percent peak area versus relative retention time (RRT) at 250 nm. While some minor changes can be noted between the control with the acid and base samples, the overall purity (peak area) of the parent molecule is just slightly higher for the acid and base sample. Some of the minor impurities appear to be reacting with the acid or base, potentially reforming to the parent. The greatest change in purity was noted in the peroxide sample where 2 major impurities were formed and the purity at 250 nm went from 98.6 to 80.6%.

TABLE 5

PRX-3140 Potassium Salt Forced Degradation Study

| RRT | Control | Acid | Base | H2O2 |
|---|---|---|---|---|
| 0.78 | | | | 8.49 |
| 0.82 | | | | 0.10 |
| 0.94 | | | 0.28 | |
| 0.99 | | 0.07 | | |
| 1.00 | 98.60 | 98.94 | 98.71 | 80.57 |
| 1.05 | <0.03 | <0.03 | <0.03 | 9.06 |
| 1.08 | 0.12 | 0.11 | 0.12 | 0.19 |
| 1.11 | 0.04 | 0.04 | | |

TABLE 5-continued

PRX-3140 Potassium Salt Forced Degradation Study

| RRT | Control | Acid | Base | H2O2 |
|---|---|---|---|---|
| 1.27 | | 0.04 | | 0.21 |
| 1.34 | 0.17 | 0.15 | 0.16 | 0.09 |
| 1.42 | | | | 0.32 |
| 1.53 | 0.42 | 0.43 | 0.42 | 0.42 |
| 1.71 | 0.23 | | | |
| 1.79 | 0.11 | 0.04 | 0.05 | 0.19 |
| 1.93 | 0.06 | | | |
| 2.51 | 0.06 | 0.06 | 0.05 | |
| 2.70 | 0.18 | 0.13 | 0.12 | 0.11 |

Acid Degradation Sample: Based on the purity peak area at 250 nm, the control was 98.6% and the acid sample was 98.9%. 1 N HCl for 24 hours had very little effect on PRX-3140 potassium salt.

Base Degradation Sample: Based on the purity peak area at 250 nm, the control was 98.6% and the base sample was 98.7%. 1 N NaOH for 24 hours had very little effect on PRX-3140 potassium salt.

Peroxide Degradation Sample: The UV chromatogram for the peroxide degradation sample at 250 nm is shown in FIG. 7A full scale. Two major impurity peaks are noted at 9.6 and 13.3 minutes (RRT 0.78 and 1.05 respectively). Based on the purity peak area at 250 nm, the control was 98.6% and the peroxide sample was 80.6%. Hydrogen peroxide, 3%, for 24 hours reacted with PRX-3140 and formed 2 major degradants.

FIG. 7B is the mass spectra of PRX-3140a at 9.6 minutes (RRT 0.78). An [M+H]+is noted at 258.0 m/z with an ammonium adduct [M+H+NH3]+ at 275.1, a sodium adduct [M+Na]+ at 280.1, and sodium dimer [2M+Na]+ at 537.1 m/z. It is noted that this is a fragile molecule and required the reduction of the Fragmentor Voltage from 150 down to 70V to see the protonated molecular ion. At the higher voltage, molecule fragments were noted at 216.0, 198.0, and 152.0. The proposed structure of PRX-3140a is Formula II: ##STR00002##, 5-hydroxy-8-(methylethyl)-8-hydro-1,2-oxathiino[6.5-b]pyridine-2,2,7-trione, or 5-hydroxy-8-(propan-2-yl)-2H-2λ6-[1,2]oxathiino[6,5-b]pyridine-2,2,7(8H)-trione with the chemical formula of C10H11NO5S and is shown in FIG. 5.

FIG. 7C is the mass spectra of PRX-3140b at 13.3 minutes (RRT 1.05). An [M+H]+ is noted at 394.2 m/z with [2M+H]+ at 787.4 m/z. This compound is noted in the control, acid, and base samples but at a very low level (<0.03%). In the peroxide sample, this peak is 9.1%. The proposed structure of PRX-3140b is Formula III: ##STR00003## [7-(methylethyl)1,4,6-trioxo(5,7-dihydrothiopheno[2,3-b]pyridine-5-yl)]-N-(3-piperidylpropyl)carboxamide, or 1,4,6-trioxo-N-[3-(piperidin-1-yl)propyl]-7-(propan-2-yl)-4,5,6,7-tetrahydro-1H-1λ4-thieno[2,3-b]pyridine-5-carboxamide with the chemical formula of C19H27N3O4S and is shown in FIG. 5.

Example 5—PRX-3140 30% Peroxide Degradation Study

Crystalline fine particle Form I of PRX-3140 potassium salt was subjected to a second forced degradation experiment using 30% hydrogen peroxide exposure for 24 hours. Sample was evaporated to dryness and analyzed using LC/UV/MS and NMR analysis. Two major degradants are noted in the LC/UV/MS.

Sample Preparation: 60 mg (55 µL) of 30% hydrogen peroxide (0.5 mmol) was added dropwise to a suspension of starting PRX-3140 potassium salt (208 mg, 0.5 mmol) in 5 mL of dry acetone at 0 degrees Celsius The resulting suspension was stirred under argon and warmed to RT spontaneously overnight (18 hours). The solvent is removed under vacuum at RT, then acetonitrile (5 mL) was added to the residue and evaporated to dryness at 40 degrees Celsius. The PRX-3140 30% peroxide sample residue weighed 300 mg.

1H NMR of the crude 30% peroxide sample is shown in FIG. 8A. For comparison, 1H NMR of PRX-3140 potassium salt is shown in FIG. 8B.

A solid portion of the PRX-3140 30% peroxide sample was submitted for LC/UV/MS analysis. Two milligrams of the sample was weighed into a 4 mL vial. Two mL of 20/80 methanol/water was added to the vial and vortexed vigorously. FIG. 9A is a HPLC chromatogram of the H2O2 sample at 250 nm. Three major peaks are noted, including the parent molecule at 12.5 minutes. A purity of 29.6% is noted for the parent molecule PRX-3140 following 18-hour exposure to 30% hydrogen peroxide. The UV spectra for the parent molecule at 12.5 min is shown in FIG. 9B. Maximums are noted at 220, 250, and 320 nm. Chromatograms for all samples were collected at all three wavelengths with 250 nm as the primary wavelength based on lambda max. FIG. 10A is the UV spectra for the peak at 8.9 minutes. In comparison with the parent molecule, the high-end absorption is absent (320 nm). FIG. 10B is the UV spectra for the peak at 12.9 minutes. The spectra are identical to the parent molecule noted in FIG. 9B. The mass spectra at 12.5 minutes for the parent molecule, PRX-3140, is shown in FIG. 11A. The protonated molecular ion, [M+H]+, is noted at 378.2 m/z. FIG. 11B is the mass spectra of PRX-3140a at 8.9 minutes (RRT 0.73 compared to 0.78 in Example 4). An [M+H]+ is noted at 258.0 m/z with [M+H+NH3]+ at 275.1, [M+Na]+ at 280.1, and [2M+Na]+ at 537.1 m/z. It is noted that this is a fragile molecule and required the reduction of the Fragmentor Voltage from 150V down to 70V to see the protonated molecular ion. At the higher voltage, molecule fragments were noted at 216.0, 198.0, and 152.0. A proposed structure of PRX-3140a is shown in FIG. 5. FIG. 11C is the mass spectra of the largest degradation product of PRX-3140b at 12.9 minutes, relative retention time (RRT) of 1.04 (compared to 1.05 in Example 4). The [M+H]+ of 394.2 m/z is potentially the parent molecule plus oxygen (+O). The proposed structure of PRX-3140B is shown in FIG. 5.

Example 6—PRX-3140 Excipient Compatibility Study

Excipient testing and compatibility studies were performed on the crystalline fine particle Form I of PRX-3140 potassium salt. We conducted excipient compatibility studies for binary blends (50:50 w/w) with the crystalline fine particle Form I of PRX-3140 potassium salt sample mixed with (1) Starch, pregelatinized, NF (Colorcon), (2) Microcrystalline Cellulose (Avicel PH-105, DuPont), (3) Magnesium Stearate NF (Avantor), (4) Stearic Acid, NF (Letco), (5) Lecithin, Granular Food Grade (Spectrum), (6) Polyethylene Glycol 3,350, USP (Dow), (7) HPB-Cyclodextrin (CTD), (8) Silicon Dioxide, FCC (Spectrum), and (9) Mannitol USP (Spectrum). Samples were analyzed by HPLC assay described in Example 2. Samples stored at 40 degrees Celsius/75% RH and assay and purity tested by LC-UV-MS at 0, 30, 60, and 90 days. At each timepoint powder samples were weighed and diluted at 50:50 methanol:DI water. Samples for HPLC analysis were filtered through a 0.45 micron PTFE filter for injection.

| Table xx Sample | Timepoint | Color | Assay PRX-3140 | % Purity PRX-3140 | PRX-3140b RRT 1.06 | % Impurities |
|---|---|---|---|---|---|---|
| Control | 0 | White | 98.8 | 98.69 | 0.03 | 1.31 |
| | 30 days | White | 100.9 | 98.74 | 0.03 | 1.26 |
| | 60 days | White | 99.5 | 98.74 | 0.03 | 1.26 |
| | 90 days | White | 100.3 | 98.63 | 0.04 | 1.27 |
| Starch | 0 | White | 100.0 | 98.79 | 0.02 | 1.21 |
| | 30 days | White-Yellow | 96.1 | 98.59 | 0.04 | 1.36 |
| | 60 days | White-Yellow | 96.2 | 98.78 | 0.05 | 1.17 |
| | 90 days | White-Yellow | 96.2 | 98.71 | 0.05 | 1.20 |
| MCC | 0 | White | 100.0 | 98.73 | 0.03 | 1.27 |
| | 30 days | White-Yellow | 99.3 | 98.72 | 0.04 | 1.28 |
| | 60 days | White-Yellow | 97.4 | 98.81 | 0.04 | 1.19 |
| | 90 days | White-Yellow | 98.9 | 98.81 | 0.05 | 1.20 |
| Magnesium Stearate | 0 | White | 100.0 | 98.76 | 0.03 | 1.24 |
| | 30 days | White | 82.2 | 98.85 | 0.05 | 1.15 |
| | 60 days | White | 83.5 | 98.93 | 0.05 | 1.17 |
| | 90 days | White | 89.4 | 98.91 | 0.05 | 1.09 |
| Stearic Acid | 0 | White | 100.0 | 98.77 | 0.03 | 1.23 |
| | 30 days | White-Yellow | 100.1 | 98.86 | 0.06 | 1.14 |
| | 60 days | White-Yellow | 94.2 | 98.90 | 0.06 | 1.02 |
| | 90 days | White-Yellow | 89.4 | 99.00 | 0.07 | 1.00 |
| Lecithin | 0 | Tan | 100.0 | 98.76 | 0.03 | 1.24 |
| | 30 days | Tan | 99.1 | 98.37 | 0.49 | 1.59 |
| | 60 days | Tan-Brown | 92.9 | 98.08 | 0.67 | 1.85 |
| | 90 days | Tan-Brown | 94.9 | 97.84 | 1.09 | 2.12 |
| PEG 3350 | 0 | White | 100.0 | 98.78 | 0.02 | 1.22 |
| | 30 days | White-Yellow | 97.1 | 98.70 | 0.05 | 1.30 |
| | 60 days | White-Yellow | 96.5 | 98.73 | 0.06 | 1.27 |
| | 90 days | White-Yellow | 94.4 | 98.57 | 0.08 | 1.30 |
| HPBCD | 0 | White | 100.0 | 98.76 | 0.02 | 1.24 |
| | 30 days | White | 96.4 | 98.76 | 0.03 | 1.24 |
| | 60 days | White | 94.1 | 98.69 | 0.03 | 1.29 |
| | 90 days | White | 94.7 | 98.75 | 0.03 | 1.15 |
| Silicon Dioxide | 0 | White | 100.0 | 98.77 | 0.03 | 1.23 |
| | 30 days | White | 93.2 | 98.74 | 0.03 | 1.26 |
| | 60 days | White | 84.6 | 98.84 | 0.03 | 1.16 |
| | 90 days | White | 85.2 | 98.89 | 0.04 | 1.10 |
| Mannitol | 0 | White | 100.0 | 98.77 | 0.02 | 1.23 |
| | 30 days | White | 96.1 | 98.77 | 0.03 | 1.23 |
| | 60 days | White | 96.2 | 98.81 | 0.03 | 1.17 |
| | 90 days | White | 96.2 | 98.57 | 0.03 | 1.20 |

The PRX-3140: lecithin (50:50) sample degraded over the 90 day study and the PRX-3140a degradation product (RRT 1.06) increased to over 1%. FIG. 12A shows the PRX-3140: lecithin (50:50) Time 0 sample and FIG. 12B shows the 90 day sample demonstrating an increase of PRX-3140B (RRT 1.05) at 90 days at 40 degrees Celsius.

Example 7—Preparation of PRX-3140 Potassium Salt PDS

A mass of 10 g of crystalline fine particle Form I of PRX-3140 potassium salt (Alchem Laboratories Corp.) and 10 g of Microcrystalline Cellulose (Avicel PH-105, DuPont) was mixed in 50 mL tube. The powder was then ground into a fine powder using a Retsch mill. Particles smaller than 600 microns were separated by sieving (30 mesh). The resulting white powder was obtained with a yield of >90% crystalline PRX-3140 potassium salt PDS powder, containing particles with a diameter less than 500 microns.

Example 8—Preparation of Immediate-Release Oral PRX-3140 Potassium Salt Capsules An immediate-release oral dosage form (gelatin capsules) containing the crystalline fine particle Form I of PRX-3140 potassium salt particles prepared in Example 7 was dry mixed with additional Microcrystalline Cellulose (Avicel PH-105, DuPont) to achieve the correct capsule fill weight (400-500 mg) to achieve the desired dose. Clear gelatin #1 capsules were then filled with the mixture in a Torpac Profill 3700 machine to yield capsules containing 320 mg of PRX-3140 potassium salt PDS with 50 mg PRX-3140. Samples were taken to verify loading uniformity, content uniformity, and dissolution time.

Example 9—Dissolution of Immediate-Release Oral PRX-3140 Potassium Salt

Capsules from Example 8 were exposed to acidic buffer for 60 minutes to mimic the stomach environment. To demonstrate dissolution, more than 75% release of PRX-3140 in solution at 15 to 30 minutes in acidic buffer was tested using a USP dissolution apparatus and HPLC.

What is claimed is:

1. A composition comprising a compound of Formula I:

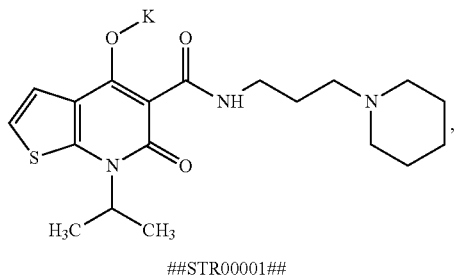

STR00001## wherein the compound of Formula I comprises a crystalline form of the compound of Formula I and wherein the composition further comprises:

(a) a compound of Formula II:

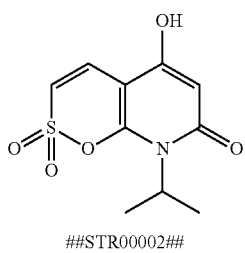

STR00002## and/or (b) a compound of Formula III:

STR00003##

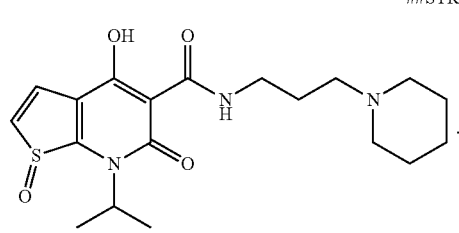

2. The composition of claim 1, wherein the crystalline form of the compound of Formula I is Form I characterized by an x-ray powder diffraction pattern comprising major peaks at 22.3+/−0.3 degrees, 25.3+/−0.3 degrees and 5.4+/−0.3 degrees two theta.

3. The composition of claim 1, wherein the crystalline form of the compound of Formula I is Form I characterized by an x-ray powder diffraction pattern comprising at least one peak selected from 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3 degrees two theta.

4. The composition of claim 1, wherein the crystalline form of the compound of Formula I is Form I characterized by an x-ray powder diffraction pattern substantially as set forth in FIG. 3A or FIG. 3B.

5. The composition of claim 1, wherein greater than 90% by weight of the compound of Formula I is the crystalline form of Form I characterized by an x-ray powder diffraction pattern comprising major peaks at 22.3+/−0.3 degrees, 25.3+/−0.3 degrees and 5.4+/−0.3 degrees two theta.

6. The composition of claim 1, wherein the compound of Formula I is the crystalline form of Form I characterized by an x-ray powder diffraction pattern comprising major peaks at 22.3+/−0.3 degrees, 25.3+/−0.3 degrees and 5.4+/−0.3 degrees two theta and is present in an amount ranging from about 0.01% to about 99.99% by mass of the composition.

7. The composition of claim 1, wherein particles of the crystalline form of the compound of Formula I have an average diameter of less than about 1 mm.

8. The composition of claim 1, wherein particles of the crystalline form of the compound of Formula I have an average diameter of less than about 500 μm.

9. The composition of claim 1, wherein the compound of Formula I is stable for at least 12 months at 5 degrees Celsius and 60% relative humidity or at 25 degrees Celsius and 60% relative humidity.

10. The composition of claim 1, wherein the composition comprises less than 0.5 weight % of the compound of Formula II, if present, and less than 0.5 weight % of the compound of Formula III, if present.

11. A particulate delivery system comprising a compound of Formula I:

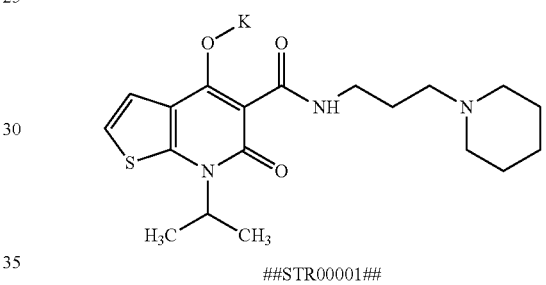

STR00001## and at least one pharmaceutically acceptable excipient, wherein the compound of Formula I comprises a crystalline form of the compound of Formula I and wherein the particulate delivery system further comprises:

(a) a compound of Formula II:

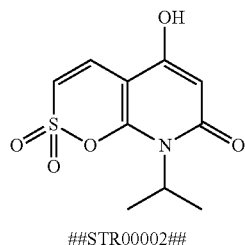 [SMILES: CC(C)n1c2c(c(O)cc1=O)C=CS(=O)(=O)O2]

STR00002## and/or (b) a compound of Formula III:

STR00003##

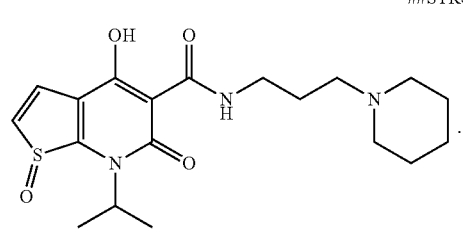

12. The particulate delivery system of claim 11, wherein the crystalline form of the compound of Formula I is Form I characterized by an x-ray powder diffraction pattern comprising major peaks at 22.3+/−0.3 degrees, 25.3+/−0.3 degrees and 5.4+/−0.3 degrees two theta.

13. The particulate delivery system of claim 11, wherein the crystalline form of the compound of Formula I is Form I characterized by an x-ray powder diffraction pattern comprising at least one peak selected from 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3 degrees two theta.

14. The particulate delivery system of claim 11, wherein the crystalline form of the compound of Formula I is Form I characterized by an x-ray powder diffraction pattern substantially as set forth in FIG. 3A or FIG. 3B.

15. The particulate delivery system of claim 11, wherein greater than 90% by weight of the compound of Formula I is the crystalline form of Form I characterized by an x-ray powder diffraction pattern comprising major peaks at 22.3+/−0.3 degrees, 25.3+/−0.3 degrees and 5.4+/−0.3 degrees two theta.

16. The particulate delivery system of claim 11, wherein the compound of Formula I is the crystalline form of Form I characterized by an x-ray powder diffraction pattern comprising major peaks at 22.3+/−0.3 degrees, 25.3+/−0.3 degrees and 5.4+/−0.3 degrees two theta and is present in an amount ranging from about 0.01% to about 99.99% by mass of the composition.

17. The particulate delivery system of claim 11, wherein particles of the crystalline form of the compound of Formula I have an average diameter of less than about 1 mm.

18. The particulate delivery system of claim 11, wherein particles of the crystalline form of the compound of Formula I have an average diameter of less than about 500 μm.

19. The particulate delivery system of claim 11, wherein the at least one pharmaceutically acceptable excipient is a polymer.

20. The particulate delivery system of claim 19, wherein the polymer is chosen from starch, cellulose, and polyethylene glycol.

21. The particulate delivery system of claim 11, wherein the particulate delivery system comprises 0.01 mg to 200 mg of the compound of Formula I.

22. The particulate delivery system of claim 11, wherein the compound of Formula I is stable for at least 12 months at 5 degrees Celsius and 60% relative humidity or at 25 degrees Celsius and 60% relative humidity.

23. The particulate delivery system of claim 11, wherein the particulate delivery system comprises less than 0.5 weight % of the compound of Formula II, if present, and less than 0.5 weight % of the compound of Formula III, if present.

24. A method of making the particulate delivery system of claim 11, comprising:
blending the compound of Formula I together with the at least one pharmaceutically acceptable excipient to form a mixture;
processing said mixture to form coarse particles having an average diameter ranging from about 0.1 mm to about 5 mm; and
grinding or milling said coarse particles to form particles having an average diameter less than about 500 μm.

25. A method of treating Alzheimer's disease (AD) and other dementias affecting the cholinergic and/or serotonergic systems, the method comprising administering an effective amount of the composition of claim 1 to a patient in need thereof.

26. A particulate delivery system comprising a compound of Formula I:

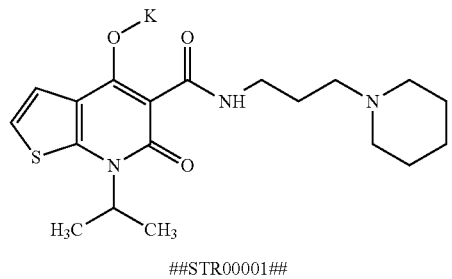

STR00001## and at least one pharmaceutically acceptable excipient, wherein the compound of Formula I comprises a crystalline form of the compound of Formula I and wherein the particulate delivery system further comprises:
(a) a compound of Formula II:

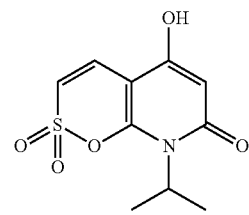

STR00002## and/or
(b) a compound of Formula III:

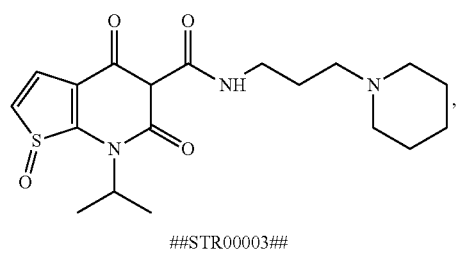 [SMILES: CC(C)N1C(=O)C(C(=O)NCCCN2CCCCC2)C(=O)C2=C1S(=O)C=C2]

STR00003## wherein the crystalline form of the compound of Formula I is Form I characterized by an x-ray powder diffraction pattern comprising at least one peak selected from 22.3+/−0.3 degrees, 25.3+/−0.3 degrees, 5.4+/−0.3 degrees, 25.8+/−0.3 degrees, 15.9+/−0.3 degrees, 29.9+/−0.3 degrees, 21.6+/−0.3 degrees, 16.5+/−0.3 degrees and 20.3 degrees two theta,
wherein greater than 90% by weight of the compound of Formula I is Form I,
wherein particles of the crystalline form of the compound of Formula I have an average diameter of less than about 500 μm,
wherein the compound of Formula I is stable for at least 12 months at 5 degrees Celsius and 60% relative humidity or at 25 degrees Celsius and 60% relative humidity,

39 and wherein the particulate delivery system is formulated for oral delivery.

27. A process for manufacturing a crystalline form of a compound of Formula I:

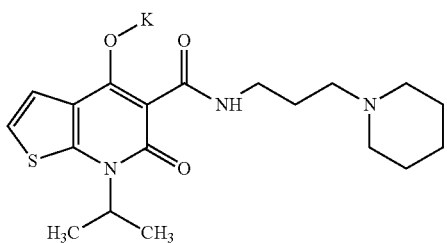

comprising the steps of:
(a) reductive amination of methyl 2-aminothiophene-3-carboxylate with sodium triacetoxyborohydride in anhydrous dichloromethane and formic acid under argon followed by potassium hydroxide and dried over Na$_2$SO$_4$ to obtain methyl 2-iso-propylaminothiophene-3-carboxylate,
(b) acylation and cyclization of methyl 2-iso-propylaminothiophene-3-carboxylate in pyridine and butyronitrile with methyl malonyl chloride followed by addition of sodium methoxide solution, washed with water and ethyl acetate, acidification with hydrochloric acid, and drying to obtain methyl 4-hydroxy-7-isopropyl-6-oxo-6,7-dihydro-thieno[2,3-b]pyridine-5-carboxylate,
(c) amidation and salt formation of methyl 4-hydroxy-7-isopropyl-6-oxo-6,7-dihydro-thieno[2,3-b]pyridine-5-carboxylate with 3-piperidin-1-yl-propylamine, dilution with water and acidification with hydrochloric acid and addition of n-butanol and MTBE to obtain 4-hydroxy-7-isopropyl-6-oxo-6,7-dihydro-thieno[2,3-b]pyridine-5-carboxylic acid (3-piperidin-1-yl-propyl)-amide hydrochloride,
(d) preparation of 4-hydroxy-7-isopropyl-6-oxo-6,7-dihydro-thieno[2,3-b]pyridine-5-carboxylic acid (3-piperidin-1-yl-propyl)-amide potassium salt by adding 4-hydroxy-7-isopropyl-6-oxo-6,7-dihydro-thieno[2,3-b]pyridine-5-carboxylic acid (3-piperidin-1-yl-propyl)-amide hydrochloride, MTBE, water, potassium hydroxide solution, and sodium bicarbonate to give 4-hydroxy-7-isopropyl-6-oxo-6,7-dihydro-thieno[2,3-b]pyridine-5-carboxylic acid (3-piperidin-1-yl-propyl)-amide to obtain the free base followed by dissolution in acetonitrile and addition of potassium hydroxide in water and acetonitrile to give crystalline 4-hydroxy-7-isopropyl-6-oxo-6,7-dihydro-thieno[2,3-b]pyridine-5-carboxylic acid (3-piperidin-1-yl-propyl)-amide potassium salt.

28. The process of claim 27, further comprising crystallization of an input 4-hydroxy-7-isopropyl-6-oxo-6,7-dihydro-thieno[2,3-b]pyridine-5-carboxylic acid (3-piperidin-1-yl-propyl)-amide free base and acetonitrile and addition of potassium hydroxide in water to provide crystalline 4-hydroxy-7-isopropyl-6-oxo-6,7-dihydro-thieno[2,3-b]pyridine-5-carboxylic acid (3-piperidin-1-yl-propyl)-amide potassium salt solid and a mother liquor followed by separation and drying, wherein greater than 90% by weight of the compound of Formula I obtained from the process is the crystalline form of the compound of Formula I.

* * * * *